US010333083B2

(12) United States Patent
Enoki

(10) Patent No.: US 10,333,083 B2
(45) Date of Patent: Jun. 25, 2019

(54) PHOTOELECTRIC CONVERSION FILM, SOLID-STATE IMAGE SENSOR, AND ELECTRONIC DEVICE

(71) Applicant: SONY SEMICONDUCTOR SOLUTIONS CORPORATION, Kanagawa (JP)

(72) Inventor: Osamu Enoki, Kanagawa (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 0 days.

(21) Appl. No.: 15/318,791

(22) PCT Filed: Apr. 16, 2015

(86) PCT No.: PCT/JP2015/061762
§ 371 (c)(1),
(2) Date: Dec. 14, 2016

(87) PCT Pub. No.: WO2015/198697
PCT Pub. Date: Dec. 30, 2015

(65) Prior Publication Data
US 2017/0141312 A1    May 18, 2017

(30) Foreign Application Priority Data

Jun. 23, 2014 (JP) ................. 2014-128425

(51) Int. Cl.
*H01L 51/00* (2006.01)
*C07F 5/02* (2006.01)
(Continued)

(52) U.S. Cl.
CPC ............ *H01L 51/008* (2013.01); *C07F 5/022* (2013.01); *H01L 51/0078* (2013.01);
(Continued)

(58) Field of Classification Search
CPC ...... H01L 51/008; H01L 27/307; C07F 5/022; H04N 5/378; H04N 9/045
(Continued)

(56) References Cited

U.S. PATENT DOCUMENTS

| 6,368,395 B1* | 4/2002 | Nohr | C07F 5/022 106/31.47 |
| 2012/0235099 A1* | 9/2012 | Ushijima | G02B 5/201 252/586 |

FOREIGN PATENT DOCUMENTS

| JP | 2001-318462 A | 11/2001 |
| JP | 2003-500510 A | 1/2003 |

(Continued)

OTHER PUBLICATIONS

International Search Report prepared by the Japan Patent Office dated Jul. 11, 2015, for International Application No. PCT/JP2015/061762.

(Continued)

*Primary Examiner* — Harold Y Pyon
*Assistant Examiner* — Danny N Kang
(74) *Attorney, Agent, or Firm* — Sheridan Ross P.C.

(57) ABSTRACT

[Object] To provide a photoelectric conversion film, a solid-state image sensor, and an electronic device which have an increased imaging characteristic.

[Solution] Provided is a photoelectric conversion film including:
a subphthalocyanine derivative represented by the following General Formula (1),
(Continued)

(A)

(B)

[Chem. 1]

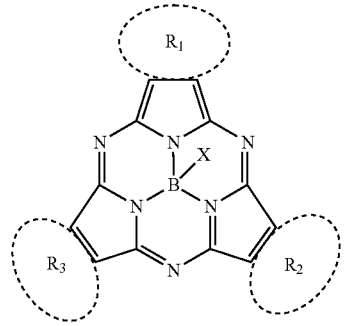

General Formula (1)

where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

12 Claims, 8 Drawing Sheets

(51) Int. Cl.
  *H04N 5/378* (2011.01)
  *H04N 9/04* (2006.01)
  *H01L 27/30* (2006.01)
  *H01L 51/42* (2006.01)

(52) U.S. Cl.
  CPC ............ *H04N 5/378* (2013.01); *H04N 9/045* (2013.01); *H01L 27/307* (2013.01); *H01L 51/4246* (2013.01)

(58) Field of Classification Search
  USPC ......................................................... 252/500
  See application file for complete search history.

(56) References Cited

FOREIGN PATENT DOCUMENTS

| | | |
|---|---|---|
| JP | 2003-234460 | 8/2003 |
| JP | 2005-303266 | 10/2005 |
| JP | 2009-538529 A | 11/2009 |
| JP | 2013-183056 A | 9/2013 |

OTHER PUBLICATIONS

Jacquot De Rouville, H.-P. et al., Synthesis and STM imaging of symmetric and dissymmetric ethynyl-bridged dimers of boron-subphthalocyanine bowl-shaped nanowheels, Chemistry—A European Journal, Jul. 16, 2012, vol. 18, Issue 29, pp. 8925-8928.

Morse, G.E. et al., Boron subphthalocyanines as organic electronic materials, ACS Applied Materials and Interfaces, Oct. 24, 2012, vol. 4, Issue 10, pp. 5055-5068.

Lee et al., "Green-Sensitive Organic Photodetectors with High Sensitivity and Spectral Selectivity Using Subphthalocyanine Derivatives," Applied Materials and Interfaces, vol. 5, 2013, pp. 13089-13095.

Official Action (with English translation) for Chinese Patent Application No. 201580020326.3, dated Dec. 11, 2018, 19 pages.

\* cited by examiner (A)

(B)

(C)

PHOTOELECTRIC CONVERSION FILM, SOLID-STATE IMAGE SENSOR, AND ELECTRONIC DEVICE

CROSS REFERENCE TO RELATED APPLICATIONS

This application is a national stage application under 35 U.S.C. 371 and claims the benefit of PCT Application No. PCT/JP2015/061762 having an international filing date of 16 Apr. 2015, which designated the United States, which PCT application claimed the benefit of Japanese Patent Application No. 2014-128425 filed 23 Jun. 2014, the disclosures of which are incorporated herein by reference in their entirety.

TECHNICAL FIELD

The present disclosure relates to a photoelectric conversion film, a solid-state image sensor, and an electronic device.

BACKGROUND ART

In recent years, as the number of pixels in solid-state image sensors has increased, sizes of pixels of the solid-state image sensor have been decreasing. However, in a planar type solid-state image sensor that is widely used, since photoelectric conversion units are two-dimensionally arranged as pixels, when sizes of pixels are reduced, areas of photoelectric conversion units are also reduced. Therefore, in the planar type solid-state image sensor, as the number of pixels increases, an aperture ratio and light collection efficiency decrease, and sensitivity decreases.

Here, in recent years, a vertical spectral type solid-state image sensor that separates light in a light incident direction by laminating photoelectric conversion units using a photoelectric conversion film formed of an organic material has been proposed.

For example, Patent Literature 1 discloses a solid-state image sensor in which organic photoelectric conversion films for absorbing each of blue light, green light and red light are laminated. In the solid-state image sensor disclosed in Patent Literature 1, a signal of each color is extracted by performing photoelectric conversion on light corresponding to that color in each of the organic photoelectric conversion films.

In addition, in Patent Literature 2, a solid-state image sensor in which an organic photoelectric conversion film that absorbs green light and a silicon photodiode are laminated is disclosed. In the solid-state image sensor disclosed in Patent Literature 2, first, a signal of green light in the organic photoelectric conversion film is extracted, a difference of a penetration depth of light in the silicon photodiode is then used to separate colors of blue light and red light, and signals of blue light and red light are extracted.

CITATION LIST

Patent Literature

| Patent Literature 1 | JP 2003-234460A |
| Patent Literature 2 | JP 2005-303266A |

SUMMARY OF INVENTION

Technical Problem

Here, in order to increase an imaging characteristic, it is necessary for a photoelectric conversion unit in a vertical spectral type solid-state image sensor to selectively absorb respective light of a specific wavelength range and transmit light other than an absorption wavelength range.

In particular, it is necessary for a photoelectric conversion unit corresponding to green light to selectively absorb green light for photoelectric conversion and sufficiently transmit blue light of a short wavelength side and red light of a long wavelength side. Specifically, a photoelectric conversion film capable of selectively absorbing green light is necessary. By using such a photoelectric conversion film, the solid-state image sensor can increase sensitivity of green light, blue light, and red light, and increase the imaging characteristic.

Therefore, the present disclosure provides a novel and improved photoelectric conversion film capable of increasing an imaging characteristic of a solid-state image sensor, a solid-state image sensor including the photoelectric conversion film, and an electronic device including the solid-state image sensor.

Solution to Problem

According to the present disclosure, there is provided a photoelectric conversion film including:

a subphthalocyanine derivative represented by the following General Formula (1),

[Chem. 1]

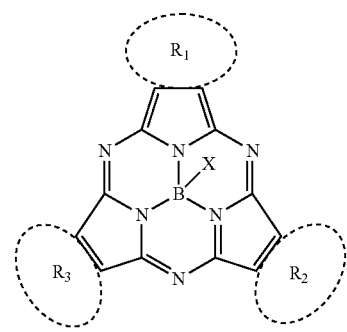

General Formula (1)

where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

According to the present disclosure, there is provided a solid-state image sensor including:

a photoelectric conversion film including a subphthalocyanine derivative represented by the above General Formula (1).

According to the present disclosure, there is provided an electronic device including:

a solid-state image sensor including a photoelectric conversion film including a subphthalocyanine derivative represented by the above General Formula (1):

an optical system configured to guide incident light to the solid-state image sensor; and an arithmetic processing circuit configured to perform arithmetic processing of an output signal from the solid-state image sensor.

According to the present disclosure, the photoelectric conversion film can selectively absorb green light and sufficiently transmit blue light and red light.

Advantageous Effects of Invention

According to the present disclosure described above, it is possible to increase an imaging characteristic of the solid-state image sensor.

Note that the effects described above are not necessarily limitative. With or in the place of the above effects, there may be achieved any one of the effects described in this specification or other effects that may be grasped from this specification.

DESCRIPTION OF EMBODIMENT(S)

Figure 1:
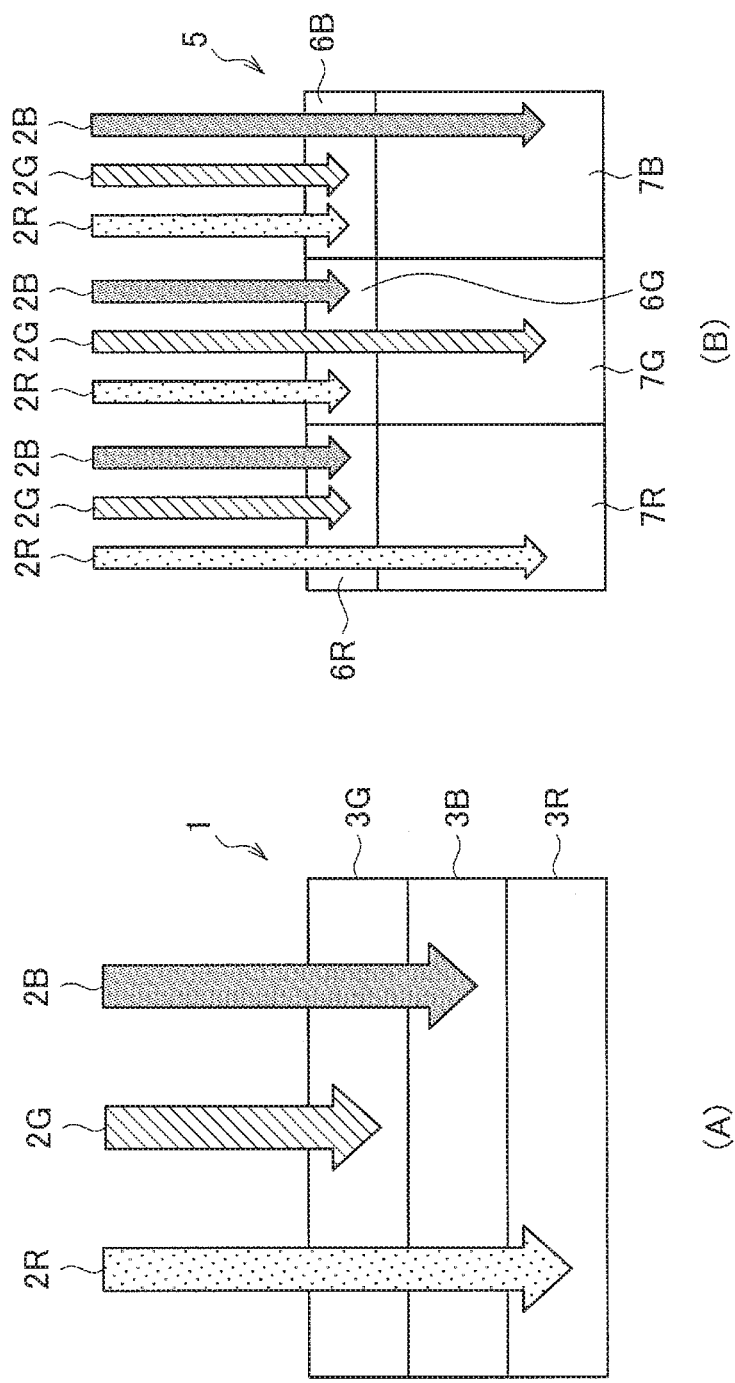
FIG. 1 shows explanatory diagrams illustrating a solid-state image sensor (A) including a photoelectric conversion element according to an embodiment of the present disclosure and a solid-state image sensor (B) according to a comparative example.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will proceed in the following order.
1. Technical background of present disclosure
2. Embodiment of present disclosure
2.1. Photoelectric conversion film according to embodiment of present disclosure
2.2. Photoelectric conversion element according to embodiment of present disclosure
2.3. Example according to embodiment of present disclosure
3. Application example of photoelectric conversion film of embodiment according to present disclosure
3.1. Configuration of solid-state image sensor
3.2. Configuration of electronic device
4. Conclusion 1. Technical Background of Present Disclosure The technological background of the present disclosure will be described with reference to FIGS. 1 and 2. FIG. 1(A) is a schematic diagram of a vertical spectral type solid-state image sensor according to an embodiment of the present disclosure. FIG. 1(B) is a schematic diagram of a planar type solid-state image sensor according to a comparative example.

Hereinafter, in this specification, when it is described that "light of a certain wavelength is absorbed," it means that about 70% or more of light of the wavelength is absorbed. In addition, in contrast, when it is described that "light of a certain wavelength is transmitted" or "light of a certain wavelength is not absorbed," it means that about 70% or more of light of the wavelength is transmitted and about 30% or less of the light is absorbed.

First, a solid-state image sensor 1 according to an embodiment of the present disclosure will be described with reference to FIG. 1(A). As illustrated in FIG. 1(A), the solid-state image sensor 1 according to an embodiment of the present disclosure has a configuration in which a green photoelectric conversion element 3G configured to absorb green light 2G, a blue photoelectric conversion element 3B configured to absorb blue light 2B and a red photoelectric conversion element 3R configured to absorb red light 2R are laminated.

For example, the green photoelectric conversion element 3G is a photoelectric conversion element that selectively absorbs green light having a wavelength of greater than or equal to 450 nm and less than 600 nm. The blue photoelectric conversion element 3B is a photoelectric conversion element that selectively absorbs blue light having a wavelength of greater than or equal to 400 nm and less than 450 nm. The red photoelectric conversion element 3R is a photoelectric conversion element that selectively absorbs red light having a wavelength of greater than or equal to 600 nm.

In the solid-state image sensor 1 according to an embodiment of the present disclosure, the blue photoelectric conversion element 3B and the red photoelectric conversion element 3R may be photodiodes that separate colors into the blue light 2B and the red light 2R using a difference of a penetration depth of light with respect to the solid-state image sensor 1. For example, the photodiodes are silicon photodiodes that absorb, for example, light having a wavelength equal to or less than 1100 nm.

Specifically, since the red light 2R has a longer wavelength so as to be less easily scattered than the blue light 2B, the red light 2R penetrates to a depth separated from a surface of incidence. On the other hand, since the blue light 2B has a shorter wavelength and is more easily scattered than the red light 2R, the blue light 2B penetrates only to a depth close to the surface of incidence. Accordingly, when the red photoelectric conversion element 3R is disposed at a position deep away from the surface of incidence of the solid-state image sensor 1, it is possible to separately detect the red light 2R from the blue light 2B. Accordingly, even when the silicon photodiode is used as the blue photoelectric conversion element 3B and the red photoelectric conversion element 3R, the blue light 2B and the red light 2R can be separated using a difference of a penetration depth of light and a signal of each color can be extracted.

Next, a planar type solid-state image sensor according to a comparative example will be described with reference to FIG. 1(B). As illustrated in FIG. 1(B), a planar type solid-state image sensor 5 includes photodiodes 7R, 7G, and 7B and color filters 6R, 6G, and 6B formed on the photodiodes 7R, 7G, and 7B.

The color filters 6R, 6G, and 6B are films that selectively transmit only light of a specific wavelength range. For example, the color filter 6R selectively transmits the red light 2R having a wavelength of greater than or equal to 600 nm, the color filter 6G selectively transmits the green light 2G having a wavelength of greater than or equal to 450 nm and less than 600 nm, and the color filter 6B selectively transmits the blue light 2B having a wavelength of greater than or equal to 400 nm and less than 450 nm.

In addition, the photodiodes 7R, 7G, and 7B are photo-detection elements configured to absorb light of a wide wavelength range. For example, the photodiodes 7R, 7G, and 7B may be silicon photodiodes configured to absorb light having a wavelength of equal to or less than 1100 nm.

Here, in the solid-state image sensor 5 shown in FIG. 1(B), since the photodiodes 7R, 7G, and 7B absorb light of a wide wavelength range, it is difficult to perform color separation with only the photodiodes 7R, 7G, and 7B. Therefore, in the solid-state image sensor 5, only light corresponding to each color is selectively transmitted by the color filters 6R, 6G, and 6B, and thus color separation is performed. Since only the red light 2R, the green light 2G, and the blue light 2B corresponding to each color are incident on the photodiodes 7R, 7G, and 7B due to the color filters 6R, 6G, and 6B, the photodiodes 7R, 7G, and 7B can extract a signal of each color.

However, in the solid-state image sensor 5 shown in FIG. 1(B), light other than light incident on the photodiodes 7R, 7G, and 7B is absorbed by the color filters 6R, 6G, and 6B. Specifically, on the photodiode 7R, only the red light 2R is incident, and the green light 2G and the blue light 2B are absorbed by the color filter 6R. In addition, on the photodiode 7C only the green light 2G is incident, and the red light 2R and the blue light 2B are absorbed by the color filter 6G. On the photodiode 7B, only the blue light 2B is incident, and the red light 2R and the green light 2G are absorbed by the color filter 6B.

Therefore, the photodiodes 7R, 7G, and 7B may substantially use only ⅓ of incident light for photoelectric conversion. Accordingly, in the solid-state image sensor 5 shown in FIG. 1(B), it was difficult to increase detection sensitivity of each color.

On the other hand, in the solid-state image sensor 1 according to an embodiment of the present disclosure, the photoelectric conversion element can selectively absorb light of a specific wavelength range corresponding to red, green, or blue. Therefore, in the solid-state image sensor 1 according to an embodiment of the present disclosure, since a color filter for performing color separation of light incident on the photoelectric conversion element is unnecessary, it is possible to use all incident light for photoelectric conversion. Accordingly, since the solid-state image sensor 1 according to an embodiment of the present disclosure can increase light that can be used for photoelectric conversion to about three times that of the solid-state image sensor 5 according to a comparative example, it is possible to further increase detection sensitivity of each color.

In the solid-state image sensor 1 according to an embodiment of the present disclosure, it is necessary for the photoelectric conversion elements 3G, 3B, and 3R to selectively absorb light of a specific wavelength range corresponding to red, green, or blue and transmit light having a wavelength other than an absorption wavelength range.

In particular, in order to increase color separation in the blue photoelectric conversion element 3B and the red photoelectric conversion element 3R that are arranged below the green photoelectric conversion element 3C it is necessary for the green photoelectric conversion element 3G to sufficiently absorb green light and sufficiently transmit blue light and red light. Specifically, it is necessary for the green photoelectric conversion element 3G to have an absorption spectrum in which a sharp peak is represented in a wavelength range of 450 nm to 600 nm.

For example, subphthalocyanine chloride (SubPc-Cl) represented by the following structural formula is proposed as a green light absorbing material in the green photoelectric conversion element 3G.

[Chem. 2]

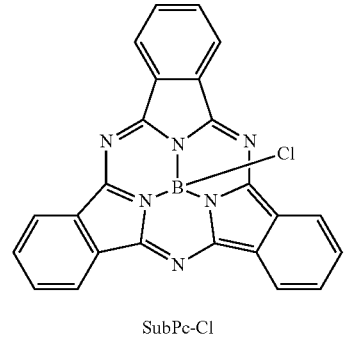

SubPc-Cl

Figure 2:
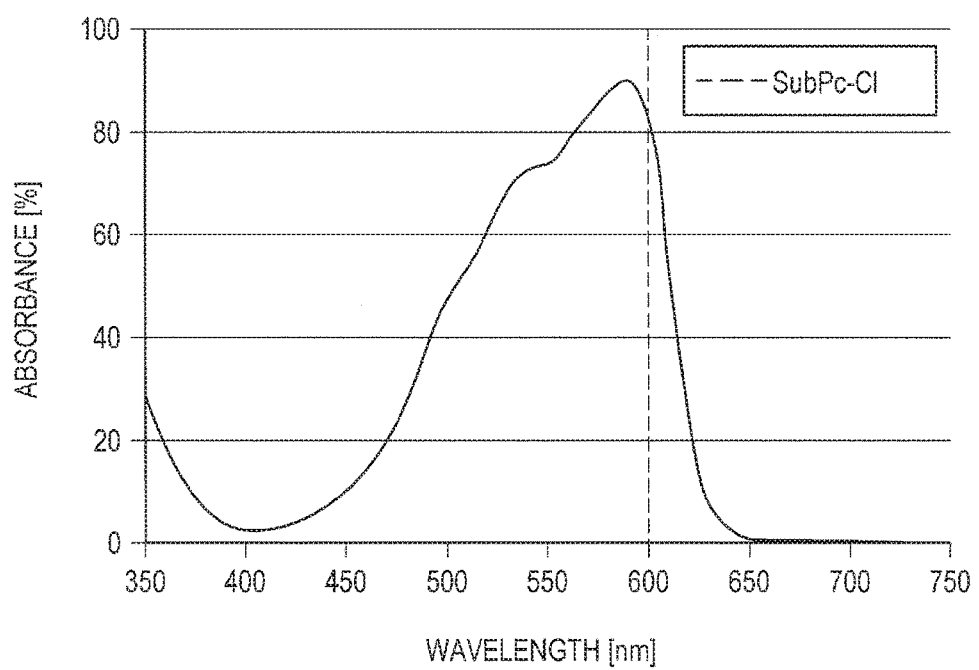
FIG. 2 is a graph showing an optical absorption spectrum of SubPc-Cl.

Here, a light absorption characteristic of SubPc-Cl is shown in FIG. 2. FIG. 2 is a graph showing an optical absorption spectrum of SubPc-Cl that is measured by a visible-ultraviolet spectrophotometer. The optical absorption spectrum of SubPc-Cl shown in FIG. 2 was measured using a sample obtained by depositing SubPc-Cl at 50 nm on a quartz substrate, and normalized such that an absorbance at a maximum absorption wavelength is 90%.

As shown in the result of FIG. 2, it can be understood that SubPc-Cl has a light absorption characteristic that a peak is generally represented on a long wavelength side, and strongly absorbs light of a longer wavelength range than green light. Specifically, it can be understood that SubPc-Cl has a maximum absorption wavelength in the vicinity of a wavelength of 600 nm and strongly absorbs light having a wavelength of greater than or equal to 600 nm. Therefore, when SubPc-Cl is used to form the green photoelectric conversion element 3G, since the green photoelectric conversion element 3G also absorbs light having a wavelength corresponding to red light, sensitivity of red light is likely to decrease in the lower red photoelectric conversion element 3R.

Therefore, it is necessary to provide a subphthalocyanine derivative appropriate for the green photoelectric conversion element 3G in which an absorption range is shown in a shorter wavelength side than SubPc-Cl and absorption of light of a long wavelength range is reduced.

In view of the above circumstances, the inventors of the present disclosure intensively studied a photoelectric conversion film appropriate for the green photoelectric conversion element 3G and completed the technology according to the present disclosure. Hereinafter, a photoelectric conversion film appropriate for the green photoelectric conversion element 3G of such a solid-state image sensor will be described.

2. Embodiment of Present Disclosure 2.1. Photoelectric Conversion Film According to Embodiment of Present Disclosure A photoelectric conversion film according to an embodiment of the present disclosure is a photoelectric conversion film including a subphthalocyanine derivative represented by the following General Formula (1).

[Chem. 3]

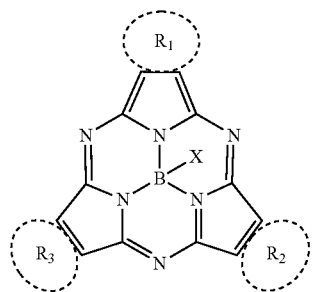

General Formula (1)

In General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

In General Formula (1), one of bonds between a boron atom at the center and nitrogen atoms is a coordinate bond.

As will be demonstrated in examples to be described, the subphthalocyanine derivative represented by General Formula (1) includes at least one hetero atom in a ring structure of $R_1$ to $R_3$, and thus can have a light absorption characteristic appropriate as a photoelectric conversion film that absorbs green light. Specifically, the subphthalocyanine derivative represented by General Formula (1) has a light absorption characteristic that absorption of light of a long wavelength range can be reduced and light of a green light range (for example, a wavelength of greater than or equal to 450 nm and less than 600) can be selectively absorbed.

In addition, in General Formula (1), at least one of $R_1$ to $R_3$ preferably has a ring structure including a substituent. Specifically, when at least one of $R_1$ to $R_3$ has a ring structure including a substituent, the subphthalocyanine derivative represented by General Formula (1) can be synthesized at a higher yield in a synthesis method to be described. In particular, in a ring structure in which at least one of $R_1$ to $R_3$ is substituted with an electron withdrawing group, since the subphthalocyanine derivative represented by General Formula (1) can be synthesized at an even higher yield, it is preferable. For example, in General Formula (1), at least one of $R_1$ to $R_3$ may have a ring structure including a halogen as a substituent.

Here, in General Formula (1), $R_1$ to $R_3$ may have a ring structure in which some hydrogen atoms are substituted with substituents or may have a ring structure in which all hydrogen atoms are substituted with substituents. In addition, the substituent may be substituted in a ring structure of $R_1$ to $R_3$ such that the subphthalocyanine derivative represented by General Formula (1) has a symmetric property or may be substituted in a ring structure of $R_1$ to $R_3$ such that the subphthalocyanine derivative represented by General Formula (1) does not have a symmetric property.

In addition, in General Formula (1), $R_1$ to $R_3$ preferably have a ring structure including a π-conjugated system structure. When $R_1$ to $R_3$ have a ring structure including a π-conjugated system structure, the subphthalocyanine derivative represented by General Formula (1) can have an absorption spectrum appropriate for absorbing green light having a wavelength of greater than or equal to 450 nm and less than 600 nm. On the other hand, when at least one of $R_1$ to $R_3$ has a ring structure without a π-conjugated system structure, in the subphthalocyanine derivative represented by General Formula (1), a length of a conjugated system of all molecules is shortened, and an absorption range significantly moves to a short wavelength side. Therefore, the subphthalocyanine derivative represented by General Formula (1) is not preferable because absorption of blue light whose wavelength range is shorter than green light increases.

In addition, in General Formula (1), $R_1$ to $R_3$ may have a ring structure including any number of ring constituent atoms. Further, $R_1$ to $R_3$ may have a single ring structure or a fused ring structure. However, preferably, $R_1$ to $R_3$ have a ring structure including 3 or more and 8 or fewer ring constituent atoms, and more preferably, a ring structure including 6 ring constituent atoms. For example, when the number of ring constituent atoms is less than 6, it is not preferable because distortion is likely to occur in the ring structure and the subphthalocyanine derivative represented by General Formula (1) is destabilized. In addition, when the number of ring constituent atoms is greater than 6, it is not preferable because a molecular weight of the subphthalocyanine derivative represented by General Formula (1) increases and handling is difficult.

Further, hetero atoms included in the ring structure of $R_1$ to $R_3$ are preferably nitrogen atoms. When the nitrogen atoms are included in the ring structure of $R_1$ to $R_3$, since an absorption range moves to a short wavelength side and absorption of light of a long wavelength range is reduced, the subphthalocyanine derivative represented by General Formula (1) can be appropriately used for a photoelectric conversion film that absorbs green light.

Hetero atoms of $R_1$ to $R_3$ to be included in the ring structure may be included in the ring structure of $R_1$ to $R_3$ such that the subphthalocyanine derivative represented by General Formula (1) has a symmetric property or may be included in the ring structure of $R_1$ to $R_3$ such that the subphthalocyanine derivative represented by General Formula (1) does not have a symmetric property.

Here, specific examples of the ring structure of the subphthalocyanine derivative represented by General Formula (1) are represented by the following Structural Examples (1) to (17). The subphthalocyanine derivative included in the photoelectric conversion film according to an embodiment of the present disclosure is a compound having a ring structure represented by the following Structural Examples (1) to (17). However, the ring structure of the subphthalocyanine derivative according to an embodiment of the present disclosure is not limited to the following Structural Examples (1) to (17).

[Chem. 4]

Structual Example (1)

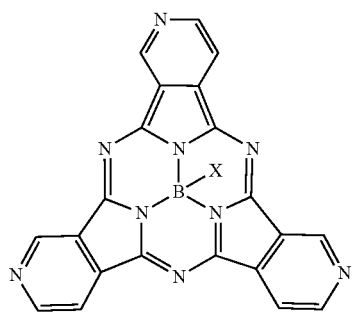

Structual Example (2)

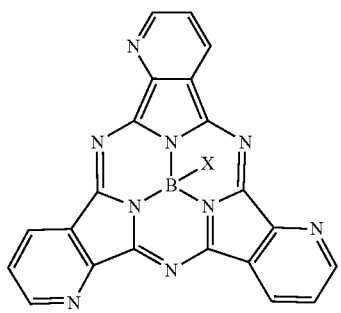

Structual Example (3)

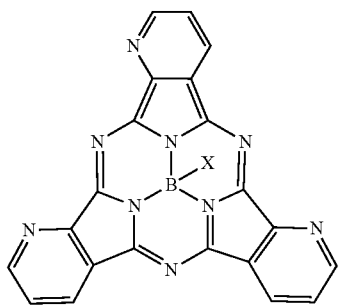

Structual Example (4)

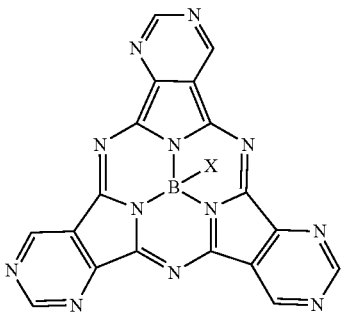

-continued

Structural Example (5)

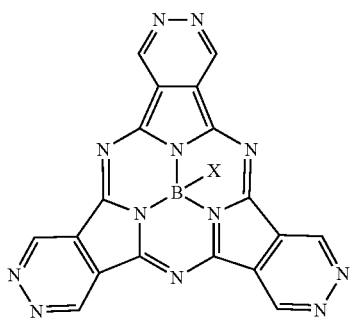

Structual Example (6)

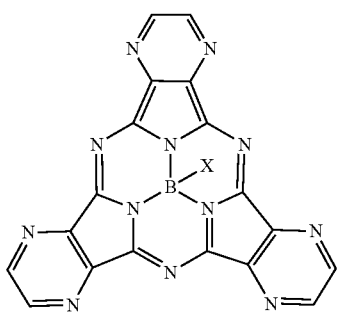

Structual Example (7)

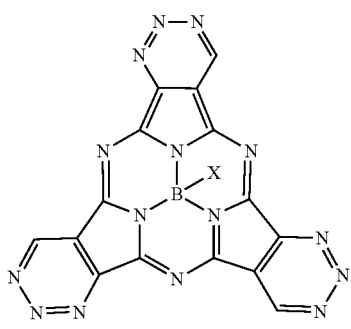

Structual Example (8)

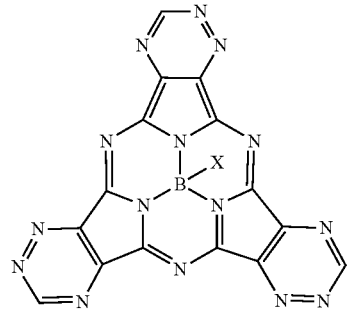

Structual Example (9)

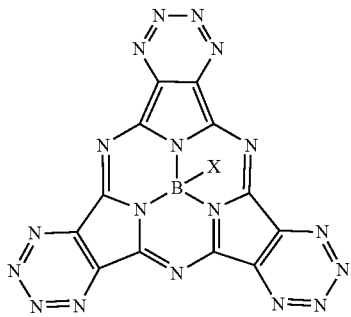

Structual Example (10)

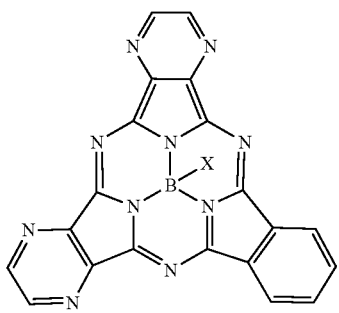

Structual Example (11)

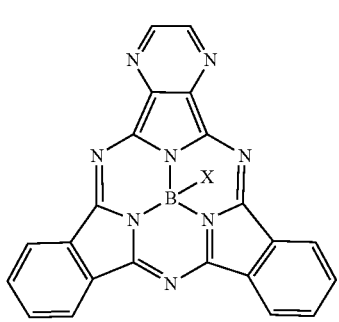

Structual Example (12)

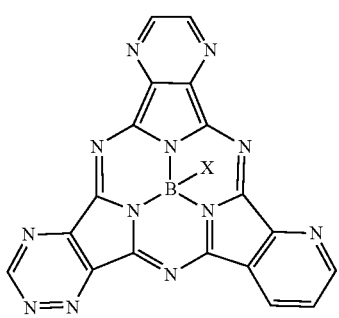

[Chem. 5]

Structual Example (13)

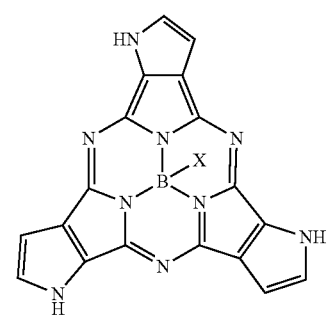

Structual Example (14)

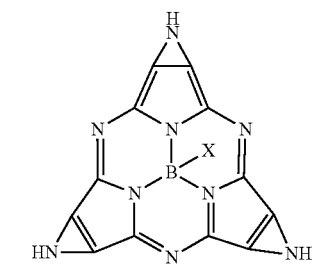

Structual Example (15)

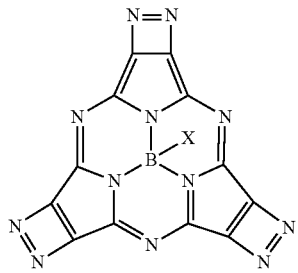

Structual Example (16)

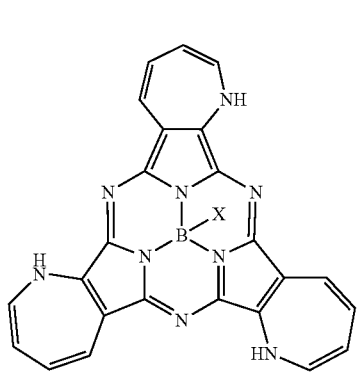

Structual Example (17)

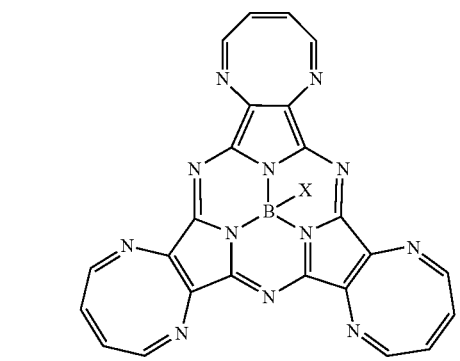

In Structural Examples (1) to (17), X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group, and a substituted or unsubstituted arylthio group.

In addition, specific compound examples of the subphthalocyanine derivative represented by General Formula (1) are represented by the following General Formulae (2) to (7). However, the subphthalocyanine derivative according to an embodiment of the present disclosure is not limited to the compound examples represented by the following General Formulae (2) to (7).

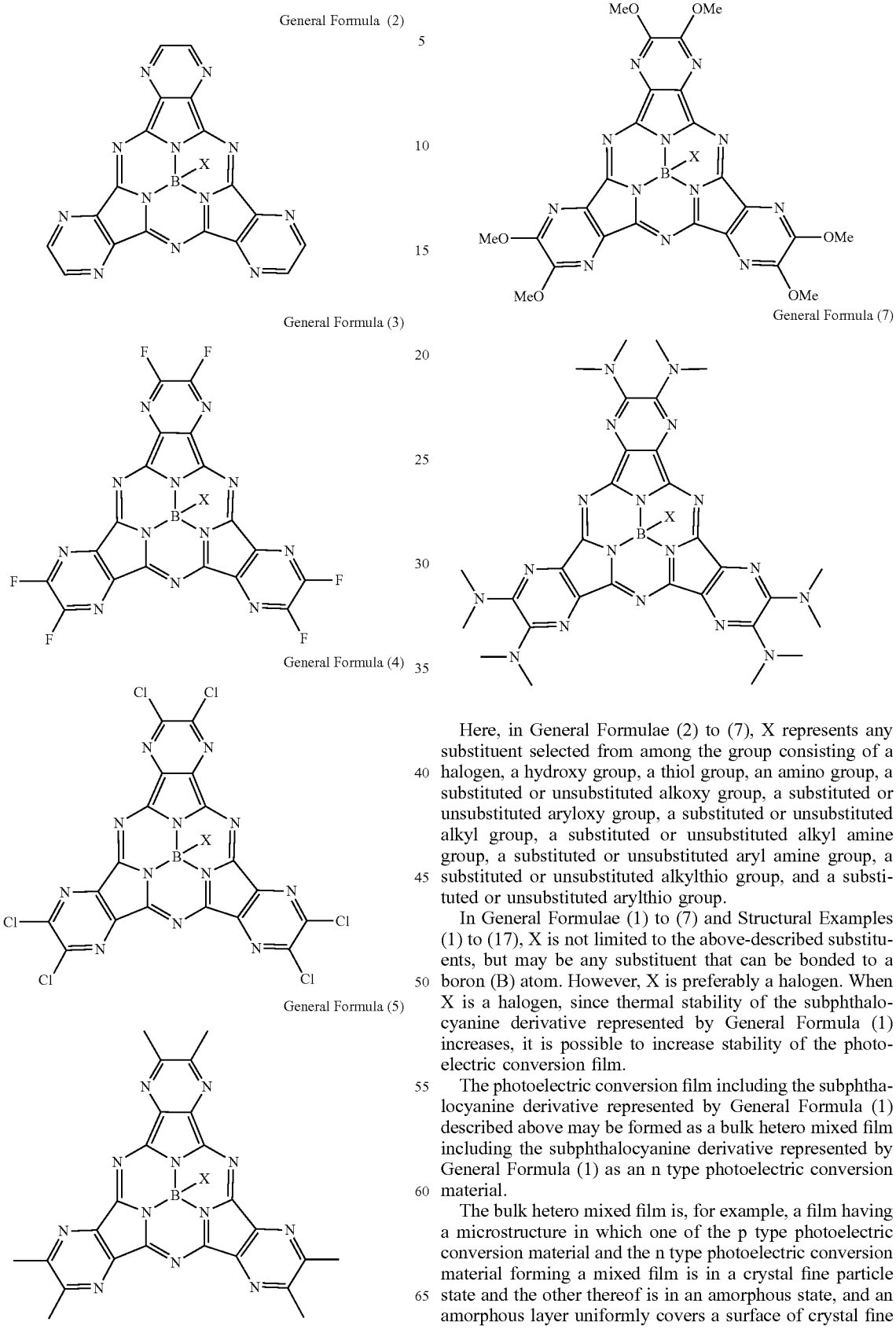

Here, in General Formulae (2) to (7), X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group, and a substituted or unsubstituted arylthio group.

In General Formulae (1) to (7) and Structural Examples (1) to (17), X is not limited to the above-described substituents, but may be any substituent that can be bonded to a boron (B) atom. However, X is preferably a halogen. When X is a halogen, since thermal stability of the subphthalocyanine derivative represented by General Formula (1) increases, it is possible to increase stability of the photoelectric conversion film.

The photoelectric conversion film including the subphthalocyanine derivative represented by General Formula (1) described above may be formed as a bulk hetero mixed film including the subphthalocyanine derivative represented by General Formula (1) as an n type photoelectric conversion material.

The bulk hetero mixed film is, for example, a film having a microstructure in which one of the p type photoelectric conversion material and the n type photoelectric conversion material forming a mixed film is in a crystal fine particle state and the other thereof is in an amorphous state, and an amorphous layer uniformly covers a surface of crystal fine particles. In such a bulk hetero mixed film, since an area of a pn junction that induces charge separation is increased by the microstructure, it induces charge separation more efficiently and increase photoelectric conversion efficiency. Alternatively, the bulk hetero mixed film may be a film having a microstructure in which both the p type photoelectric conversion material and the n type photoelectric conversion material forming a film are in a fine crystalline state and mixed.

In the photoelectric conversion film according to an embodiment of the present disclosure, when the subphthalocyanine derivative represented by General Formula (1) is included as the n type photoelectric conversion material, various compounds having a charge transporting characteristic can be used as a compound to be included as the p type photoelectric conversion material.

Specifically, the p type photoelectric conversion material included in the photoelectric conversion film according to an embodiment of the present disclosure preferably has at least one of a hole transporting characteristic and an electron transporting characteristic regardless of an absorption wavelength. For example, the p type photoelectric conversion material may be a quinacridone derivative, a phthalocyanine derivative, a porphyrin derivative, a squarylium derivative, a naphthalene or perylene derivative, a cyanine derivative, a merocyanine derivative, a rhodamine derivative, a diphenylmethane or triphenylmethane derivative, a xanthene derivative, an acridine derivative, a phenoxazine derivative, a quinoline derivative, an oxazole derivative, a thiazole derivative, an oxazine derivative, a thiazine derivative, a benzoquinone derivative, a naphthoquinone derivative, an anthraquinone derivative, an indigo or thioindigo derivative, a pyrrole derivative, a pyridine derivative, a jipirin derivative, an indole derivative, a diketopyrrolopyrrole derivative, a coumarin derivative, a fluorene derivative, a fluoranthene derivative, an anthracene derivative, a pyrene derivative, a triarylamine derivative such as triphenylamine, naphthylamine or styrylamine, a carbazole derivative, a phenylenediamine derivative or a benzidine derivative, a phenanthroline derivative, an imidazole derivative, an oxazoline derivative, a thiazoline derivative, a triazole derivative, a thiadiazole derivative, an oxadiazole derivative, a thiophene derivative, a selenophene derivative, a silole derivative, a germole derivative, a stilbene derivative or a phenylene vinylene derivative, a pentacene derivative, a rubrene derivative, a thienothiophene derivative, a benzodithiophene derivative, a xanthenoxanthene derivative, or a fullerene derivative. In addition, the p type photoelectric conversion material may be a connecting body having the above-described substituent as a unit structure, a monomer, a polymer, a copolymer or a block copolymer. In particular, quinacridone derivatives are preferable as the p type photoelectric conversion material included in the photoelectric conversion film according to an embodiment of the present disclosure.

In addition, the photoelectric conversion film according to an embodiment of the present disclosure may be a planar heterojunction film in which the subphthalocyanine derivative represented by General Formula (1) serving as the n type photoelectric conversion material and the p type photoelectric conversion material are laminated to form a heterojunction. It is needless to say that the photoelectric conversion film according to an embodiment of the present disclosure may include the subphthalocyanine derivative represented by General Formula (1) as the p type photoelectric conversion material.

Further, the photoelectric conversion film according to an embodiment of the present disclosure may be formed as a monolayer film that includes only the subphthalocyanine derivative represented by General Formula (1).

As described above, when the photoelectric conversion film according to an embodiment of the present disclosure includes the subphthalocyanine derivative represented by General Formula (1), it is possible to reduce absorption of light of a long wavelength range and selectively absorb green light. Accordingly, the photoelectric conversion film according to an embodiment of the present disclosure is appropriate as the green photoelectric conversion element of the solid-state image sensor and improves color separation of each color of light. Therefore, it is possible to increase sensitivity of the solid-state image sensor and increase an imaging characteristic.

Figure 3:
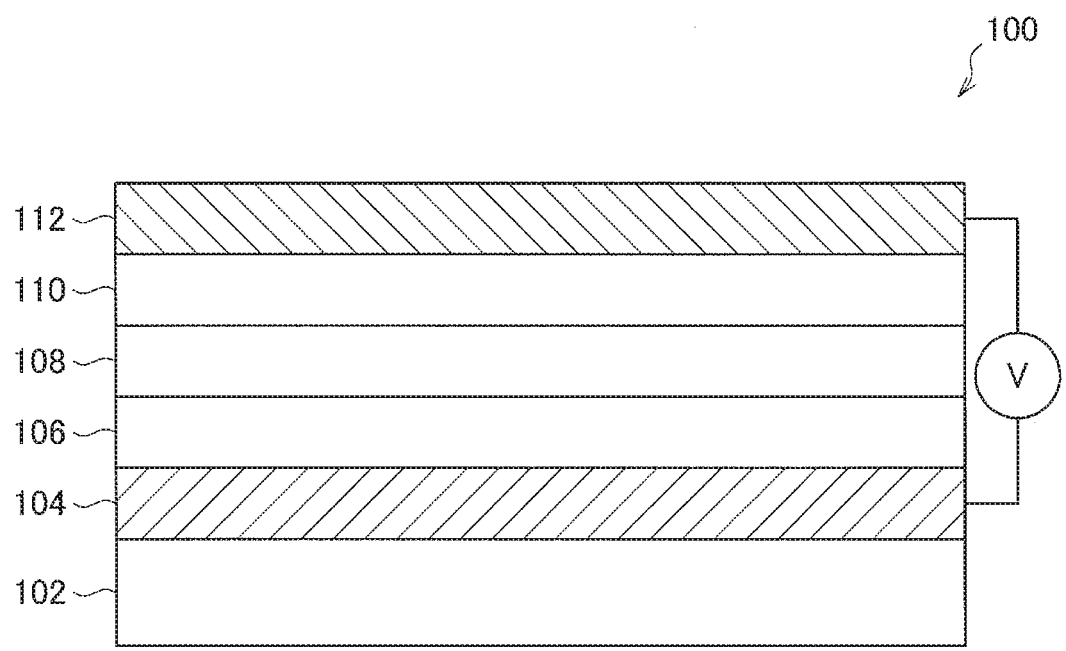
FIG. 3 is a schematic diagram illustrating an exemplary photoelectric conversion element according to an embodiment of the present disclosure.

2.2. Photoelectric Conversion Element According to Embodiment of Present Disclosure Next, a photoelectric conversion element according to an embodiment of the present disclosure will be described with reference to FIG. 3. FIG. 3 is a schematic diagram illustrating an exemplary photoelectric conversion element according to an embodiment of the present disclosure.

As illustrated in FIG. 3, a photoelectric conversion element 100 according to an embodiment of the present disclosure includes a substrate 102, a lower electrode 104 arranged above the substrate 102, a p buffer layer 106 arranged above the lower electrode 104, a photoelectric conversion layer 108 arranged above the p buffer layer 106, an n buffer layer 110 arranged above the photoelectric conversion layer 108, and an upper electrode 112 arranged above the n buffer layer 110.

A structure of the photoelectric conversion element 100 shown in FIG. 3 is only an example, and the structure of the photoelectric conversion element 100 according to an embodiment of the present disclosure is not limited to the structure shown in FIG. 3. For example, at least one of the p buffer layer 106 and the n buffer layer 110 may be omitted.

The substrate 102 is a support in which layers forming the photoelectric conversion element 100 are laminated and disposed. As the substrate 102, a substrate used in a general photoelectric conversion element may be used. For example, the substrate 102 may be various types of glass substrates such as a high strain point glass substrate, a soda glass substrate and a borosilicate glass substrate, a quartz substrate, a semiconductor substrate, and a plastic substrate such as a polymethylmethacrylate, polyvinyl alcohol, polyimide or polycarbonate substrate. In the photoelectric conversion element 100, when incident light is transmitted to an opposite side, the substrate 102 is preferably formed of a transparent material.

The lower electrode 104 and the upper electrode 112 are formed of a conductive material. In addition, the lower electrode 104 is arranged above the substrate 102 and the upper electrode 112 is arranged above the n buffer layer 110. Specifically, at least one of the lower electrode 104 and the upper electrode 112 is formed of a transparent conductive material such as indium tin oxide (ITO) or indium zinc oxide (IZO). When incident light is transmitted to an opposite side in the photoelectric conversion element 100, both the lower electrode 104 and the upper electrode 112 are preferably formed of a transparent conductive material such as ITO.

As the transparent conductive material, tin oxide (TO), a tin oxide ($SnO_2$)-based material in which a dopant is added or a zinc oxide-based material in which a dopant is added to zinc oxide (ZnO) may be used. As the zinc oxide-based material, for example, aluminum zinc oxide (AZO) in which aluminum (Al) is added as a dopant, gallium zinc oxide (GZO) in which gallium (Ga) is added, and indium zinc oxide (IZO) in which indium (In) is added can be exemplified. In addition thereto, as the transparent conductive material, CuI, InSbO$_4$, ZnMgO, CuInO$_2$, MgIN$_2$O$_4$, CO, ZnSnO$_3$ or the like may be used. Further, as the transparent conductive material, indium gallium zinc oxide (IGZO), indium gallium oxide (IGO), aluminum gallium zinc oxide (AGZO), graphene, a metallic thin film, and PEDOT may be used.

Further, a bias voltage is applied to the lower electrode 104 and the upper electrode 112. For example, the bias voltage is applied to set a polarity such that electrons move to the upper electrode 112 and holes move to the lower electrode 104 among charges generated in the photoelectric conversion layer 108.

In addition, it is needless to say that the bias voltage may be applied to set a polarity such that holes move to the upper electrode 112 and electrons move to the lower electrode 104 among charges generated in the photoelectric conversion layer 108. In this case, in the photoelectric conversion element 100 illustrated in FIG. 3, positions of the p-buffer layer 106 and the n-buffer layer 110 are switched.

The p buffer layer 106 is a layer that is arranged above the lower electrode 104 and provides a function of extracting a hole from the photoelectric conversion layer 108 with high efficiency. Specifically, the p buffer layer 106 includes the p type photoelectric conversion material having at least one of a hole transporting characteristic and an electron transporting characteristic. As the p type photoelectric conversion material, for example, a quinacridone derivative, a phthalocyanine derivative, a porphyrin derivative, a squarylium derivative, a naphthalene or perylene derivative, a cyanine derivative, a merocyanine derivative, a rhodamine derivative, a diphenylmethane or triphenylmethane derivative, a xanthene derivative, an acridine derivative, a phenoxazine derivative, a quinoline derivative, an oxazole derivative, a thiazole derivative, an oxazine derivative, a thiazine derivative, a benzoquinone derivative, a naphthoquinone derivative, an anthraquinone derivative, an indigo or thioindigo derivative, a pyrrole derivative, a pyridine derivative, a jipirin derivative, an indole derivative, a diketopyrrolopyrrole derivative, a coumarin derivative, a fluorene derivative, a fluoranthene derivative, an anthracene derivative, a pyrene derivative, a triarylamine derivative such as triphenylamine, naphthylamine or styrylamine, a carbazole derivative, a phenylenediamine derivative or a benzidine derivative, a phenanthroline derivative, an imidazole derivative, an oxazoline derivative, a thiazoline derivative, a triazole derivative, a thiadiazole derivative, an oxadiazole derivative, a thiophene derivative, a selenophene derivative, a silole derivative, a germole derivative, a stilbene derivative or a phenylene vinylene derivative, a pentacene derivative, a rubrene derivative, a thienothiophene derivative, a benzodithiophene derivative, a xanthenoxanthene derivative, or a fullerene derivative can be exemplified. In addition, the p type photoelectric conversion material may be a connecting body having the above-described substituent as a unit structure, a monomer, a polymer, a copolymer or a block copolymer. A wavelength band of light that the p type photoelectric conversion material absorbs is not particularly limited and may be any wavelength band.

More specifically, the p buffer layer 106 may be formed of a hole transporting material and may be formed of an arylamine, oxazole, oxadiazole, triazole, imidazole, stilbene, a polyarylalkane, porphyrin, anthracene, fluorenone, hydrazine or derivatives thereof. For example, the p buffer layer 106 may be formed of N,N'-bis(3-methylphenyl)-(1,1'-biphenyl)-4,4'-diamine (TPD), 4,4'-bis[N-(naphthyl)-N-phenylamino]biphenyl(α-NPD), 4,4',4"-tris(N-(3-methylphenyl)N-phenylamino)triphenylamine (m-MTDATA), tetraphenylporphyrin copper, phthalocyanine, or copper phthalocyanine.

The photoelectric conversion layer 108 is a layer that is arranged above the p buffer layer 106 and provides a function of selectively absorbing green light (for example, light having a wavelength of greater than or equal to 450 nm and less than 600 nm) and photoelectrically converting the absorbed light. In the photoelectric conversion element according to an embodiment of the present disclosure, the photoelectric conversion layer 108 includes the above-described subphthalocyanine derivative represented by General Formula (1). For example, the photoelectric conversion layer 108 may be a bulk hetero mixed film that includes the subphthalocyanine derivative represented by General Formula (1) as the n type photoelectric conversion material and a quinacridone derivative as the p type photoelectric conversion material.

The photoelectric conversion layer 108 may be formed as a single layer in which the n type photoelectric conversion material and the p type photoelectric conversion material are mixed at a single ratio. In addition, the photoelectric conversion layer 108 may be formed of a plurality of layers in which the mixing ratio of the n type photoelectric conversion material and the p type photoelectric conversion material is changed in a lamination direction. For example, the photoelectric conversion layer 108 may have a multilayer structure in which a p layer formed of the p type photoelectric conversion material from the p buffer layer 106 side, an i layer in which the n type photoelectric conversion material and the p type photoelectric conversion material are mixed, and an n layer formed of the n type photoelectric conversion material are laminated.

In the photoelectric conversion element according to an embodiment of the present disclosure, as long as the subphthalocyanine derivative represented by General Formula (1) is included, the photoelectric conversion layer 108 is not limited to the bulk hetero mixed film, and may be formed of a monolayer film, a planar heterojunction film, or the like.

The n buffer layer 110 is a layer that is arranged above the photoelectric conversion layer 108 and provides a function of extracting electrons from the photoelectric conversion layer 108 with high efficiency. Specifically, the n buffer layer 110 is formed of an electron transporting material, and may be formed of, for example, fullerenes, carbon nanotubes, oxadiazole, a triazole compound, anthraquinodimethane, diphenyl quinone, a distyrylarylene, a silole compound or derivatives thereof. Specifically, the n buffer layer 110 may be formed of 1,3-bis(4-tert-butylphenyl-1,3,4-oxadiazolyl) phenylene (OXD-7), bathocuproine, bathophenanthroline, or tris(8-hydroxyquinolinate)aluminum (Alq3).

In addition, in the structure of the photoelectric conversion element 100 illustrated in FIG. 3, materials forming layers other than the photoelectric conversion layer 108 are not specifically limited, but a known material for the photoelectric conversion element may also be used.

Here, each of the layers in the photoelectric conversion element 100 according to an embodiment of the present disclosure described above may be formed by an appropriate film formation method that is selected according to a material such as a vacuum deposition, a sputtering, and various coating methods.

For example, in each of the layers forming the photoelectric conversion element 100 according to an embodiment of the present disclosure, the lower electrode 104 and the upper electrode 112 may be formed by a deposition method including an electron beam deposition method, a hot filament deposition method and a vacuum deposition method, a sputtering method, a combination of a chemical vapor deposition method (CVD method), an ion plating method and an etching method, various types of printing methods such as a screen printing method, an ink jet printing method and a metal mask printing method, or a plating method (an electroplating method and an electroless plating method), and the like.

In addition, in each of the layers forming the photoelectric conversion element 100 according to an embodiment of the present disclosure, each layer such as the p-buffer layer 106, the photoelectric conversion layer 108 and the n-buffer layer 110 may be formed by, for example, the deposition method such as the vacuum deposition method, the printing method such as the screen printing method and the ink jet printing method, a laser transfer method and the coating method such as a spin coating method.

An exemplary configuration of the photoelectric conversion element 100 according to an embodiment of the present disclosure has been described above.

2.3. Example According to Embodiment of Present Disclosure

Hereinafter, the subphthalocyanine derivative, the photoelectric conversion film and the photoelectric conversion element according to an embodiment of the present disclosure will be described in detail with reference to examples and comparative examples. However, the following examples are only examples and the photoelectric conversion film and the photoelectric conversion element according to an embodiment of the present disclosure are not limited to the following examples.

[Simulation Analysis]

First, spectral characteristics of the subphthalocyanine derivative according to an embodiment of the present disclosure were evaluated by simulation analysis. Specifically, the simulation analysis was performed on the subphthalocyanine derivatives represented by the following structural formula and a maximum absorption wavelength $\lambda_{max}$ was calculated. For comparison, the simulation analysis was performed on subphthalocyanine derivatives (SubPc-Cl, SubPc-F) according to a comparative example, and a maximum absorption wavelength $\lambda_{max}$ was calculated.

[Chem. 7]

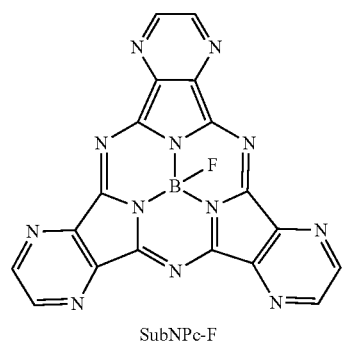

SubNPc-F

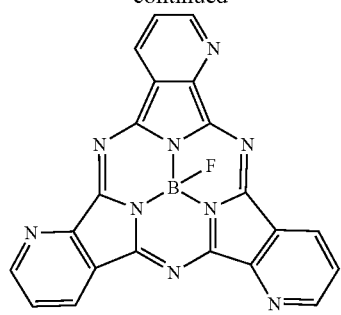

pyri-SubNPc-F

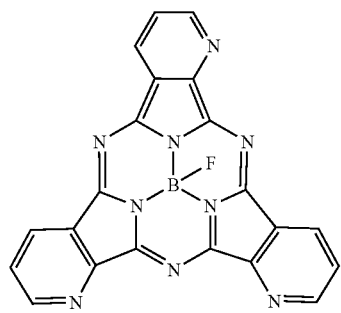

isopyri-SubNPc-F

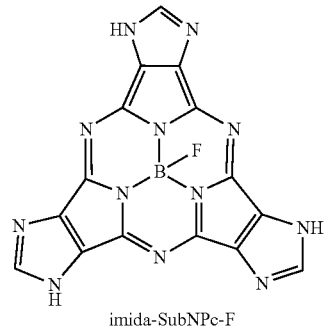

imida-SubNPc-F

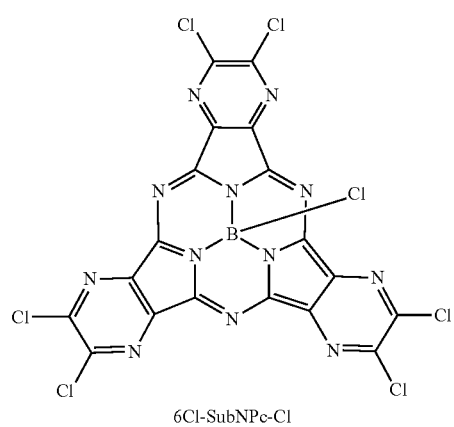

6Cl-SubNPc-Cl

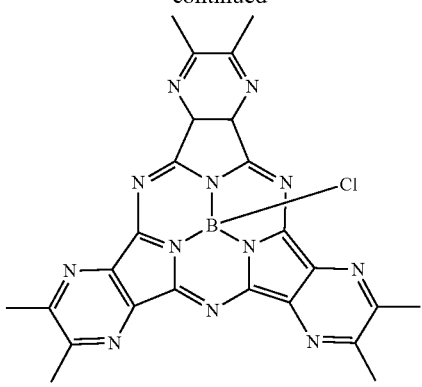

6Me-SubNPc-Cl

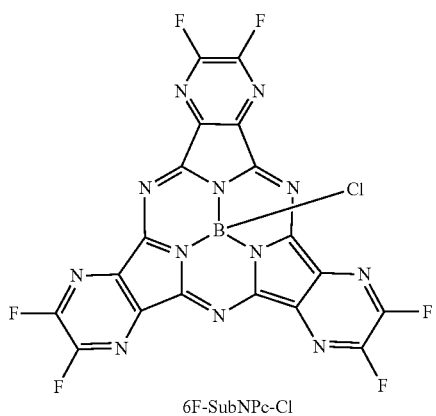

6F-SubNPc-Cl

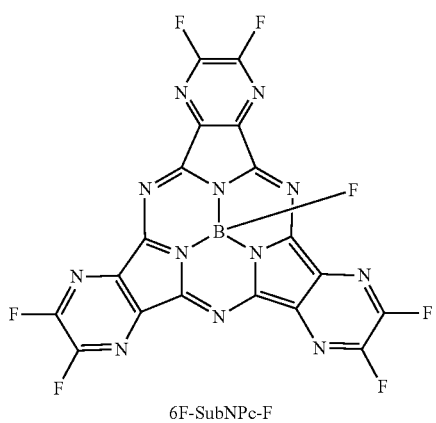

6F-SubNPc-F

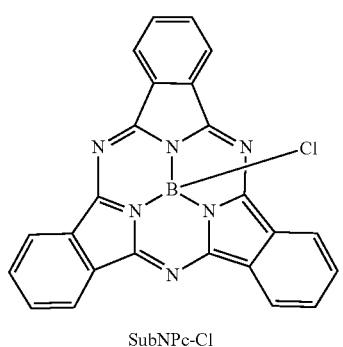

SubNPc-Cl

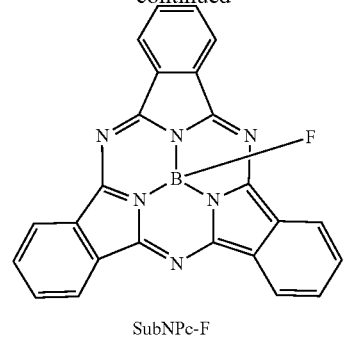

SubNPc-F

In the simulation analysis, molecular orbital calculation using density functional theory (DFT) was used, Gaussian03 was used as a calculation program, and "6-311++G" was used as a basis function at the functional level of "B3LYP."

Specifically, first, structure optimization calculation was performed on each of the subphthalocyanine derivatives by a self-consistent field (SCF) and an energy level of each molecular orbital was computed. Next, time-dependent density functional theory (TD-DFT) was applied, an ultraviolet-visible absorption (UV-VIS) spectrum was calculated, and a maximum absorption wavelength was computed.

The maximum absorption wavelengths $\lambda_{max}$ of each of the subphthalocyanine derivatives computed by the simulation analysis are shown in the following Table 1. Since the maximum absorption wavelengths $\lambda_{max}$ of the subphthalocyanine derivatives shown in Table 1 are simulation analysis results in a single molecule, absolute values thereof do not match actual measurement values of absorption spectrums that were actually measured in a solution which will be described. However, as can be understood from actual measurement values of absorption spectrums in a solution which will be described, tendencies of the following simulation analysis results and the actual measurement results match.

[Table 1]

TABLE 1

|  |  | $\lambda_{max}$ [nm] |
| --- | --- | --- |
| Example 1 | SubNPc-F | 456.8 |
| Example 2 | pyri-SubNPc-F | 463.8 |
| Example 3 | isopyri-SubNPc-F | 466.7 |
| Example 4 | imida-SubNPc-F | 431.1 |
| Example 5 | 6Cl-SubNPc-Cl | 464.3 |
| Example 6 | 6Me-SubNPc-Cl | 459.4 |
| Example 7 | 6F-SubNPc-Cl | 458.3 |
| Example 8 | 6F-SubNPc-F | 460.6 |
| Comparative Example 1 | SubPc-Cl | 496.0 |
| Comparative Example 2 | SubPc-F | 499.5 |

As shown in the results in Table 1, it can be understood that subphthalocyanine derivatives according to Examples 1 to 8 have a shorter maximum absorption wavelength $\lambda_{max}$ and have more reduced absorption of light of a long wavelength range than subphthalocyanine derivatives according to Comparative Examples 1 and 2.

Specifically, comparing Example 1 and Comparative Examples 1 and 2, it can be understood that, regardless of a substituent that is bonded to a boron atom at the center, when a nitrogen atom serving as a hetero atom is introduced into the ring structure of $R_1$ to $R_3$ in General Formula (1), $\lambda_{max}$ becomes a short wavelength. In addition, comparing Examples 1 and 5 to 7, it can be understood that, even if a substituent is introduced into the ring structure of $R_1$ to $R_3$ in General Formula (1), similarly, $\lambda_{max}$ becomes a shorter wavelength. Further, comparing Examples 1 to 4, it can be understood that, regardless of the number of ring constituent atoms of the ring structure of $R_1$ to $R_3$ in General Formula (1) and regardless of the number of hetero atoms included in the ring structure of $R_1$ to $R_3$ and positions thereof, $\lambda_{max}$ becomes a shorter wavelength.

Accordingly, it can be understood that, in the subphthalocyanine derivative according to an embodiment of the present disclosure, at least one hetero atom is included in the ring structure of at least one of $R_1$ to $R_3$ in General Formula (1), and thus a maximum absorption wavelength can become a shorter wavelength.

[Synthesis of Subphthalocyanine Derivative]

Next, a method of synthesizing the subphthalocyanine derivative according to an embodiment of the present disclosure will be described. The subphthalocyanine derivative according to an embodiment of the present disclosure can be synthesized by a generalized synthesis method represented by the following Reaction Formula 1. The synthesis method to be described is only an example, and the method of synthesizing the subphthalocyanine derivative according to an embodiment of the present disclosure is not limited to the following example.

[Chem. 8]

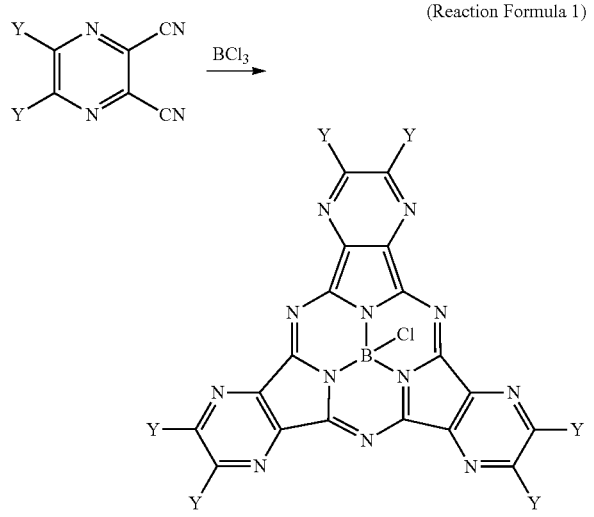

(Reaction Formula 1)

As shown in Reaction Formula 1, when 2,3-dicyanopyrazine derivatives and boron trichloride are mixed in a solvent and heated to reflux, it is possible to synthesize the subphthalocyanine derivative according to an embodiment of the present disclosure. In Reaction Formula 1, while substituents Y substituted in 2,3-dicyanopyrazine derivatives are described as the same substituents, it is needless to say that the substituents Y in 2,3-dicyanopyrazine derivatives may be different from each other.

Further, a specific method of synthesizing the subphthalocyanine derivative according to an embodiment of the present disclosure will be described by exemplifying specific compounds.

Synthesis of SubNPc-Cl

SubNPc-Cl represented by the following structural formula was synthesized by the following method.

[Chem. 9]

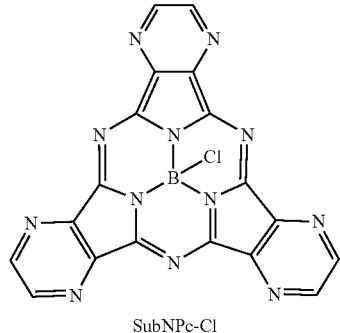

SubNPc-Cl 2,3-dicyanopyrazine (in Reaction Formula 1, Y=H) at 3 mmol and boron trichloride (a dichloromethane solution) at 1 mmol (1 ml) were added into a flask, and heated to reflux using 3 ml of I-chloro-naphthalene in a solvent. A Dimroth cooler was connected to the mouth of the flask, an upper portion of the Dimroth cooler was additionally guided to an exhaust port of a draft by a rubber tube, and a low boiling point component was gradually evaporated. The flask had a bath temperature that was set to 190° C. and heated to reflux for about 16 hours.

After being heated to reflux, the mixture was left overnight, filtered, and further washed with dichloromethane. A filtrate was purified by column chromatography and thus 6 mg of a red component SubNPc-Cl (yield 1.3%) was obtained. When $^1$H-nuclear magnetic resonance (NMR) measurement was performed on the obtained SubNPc-Cl in a $CDCl_3$ solvent, it was determined that a main peak was in one singlet ($\delta$=9.240) in an aromatic region, and a reaction product was SubNPc-Cl.

Synthesis of 6Cl-SubNPc-Cl

In addition, according to a synthesis method similar to that of SubNPc-Cl, 6Cl-SubNPc-Cl represented by the following structural formula was synthesized.

[Chem. 10]

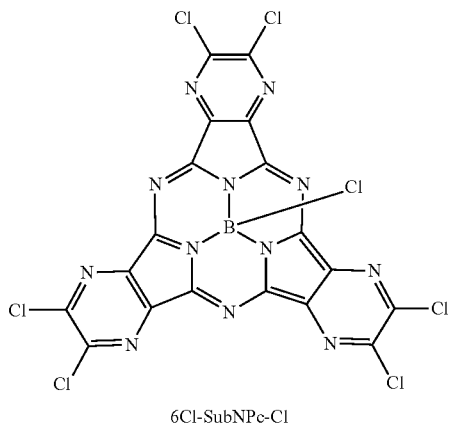

6Cl-SubNPc-Cl

Synthesis of the above SubNPc-Cl was performed by a similar method except that 5,6-dichloro-2,3-dicyanopyrazine (in Reaction Formula 1, Y=Cl) was used as a starting material in place of 2,3-dicyanopyrazine, and 6Cl-SubNPc-Cl was obtained. A yield of 6Cl-SubNPc-Cl was 11%.

Synthesis of 2Cl-SubNPc-Cl, 4Cl-SubNPc-Cl

In addition, for example, by a synthesis method represented by the following Reaction Formula 2, it is possible to synthesize subphthalocyanine derivatives (2Cl-SubNPc-Cl and 4Cl-SubNPc-Cl) having different ring structures of $R_1$ to $R_3$.

[Chem. 11]

(Reaction Formula 2)

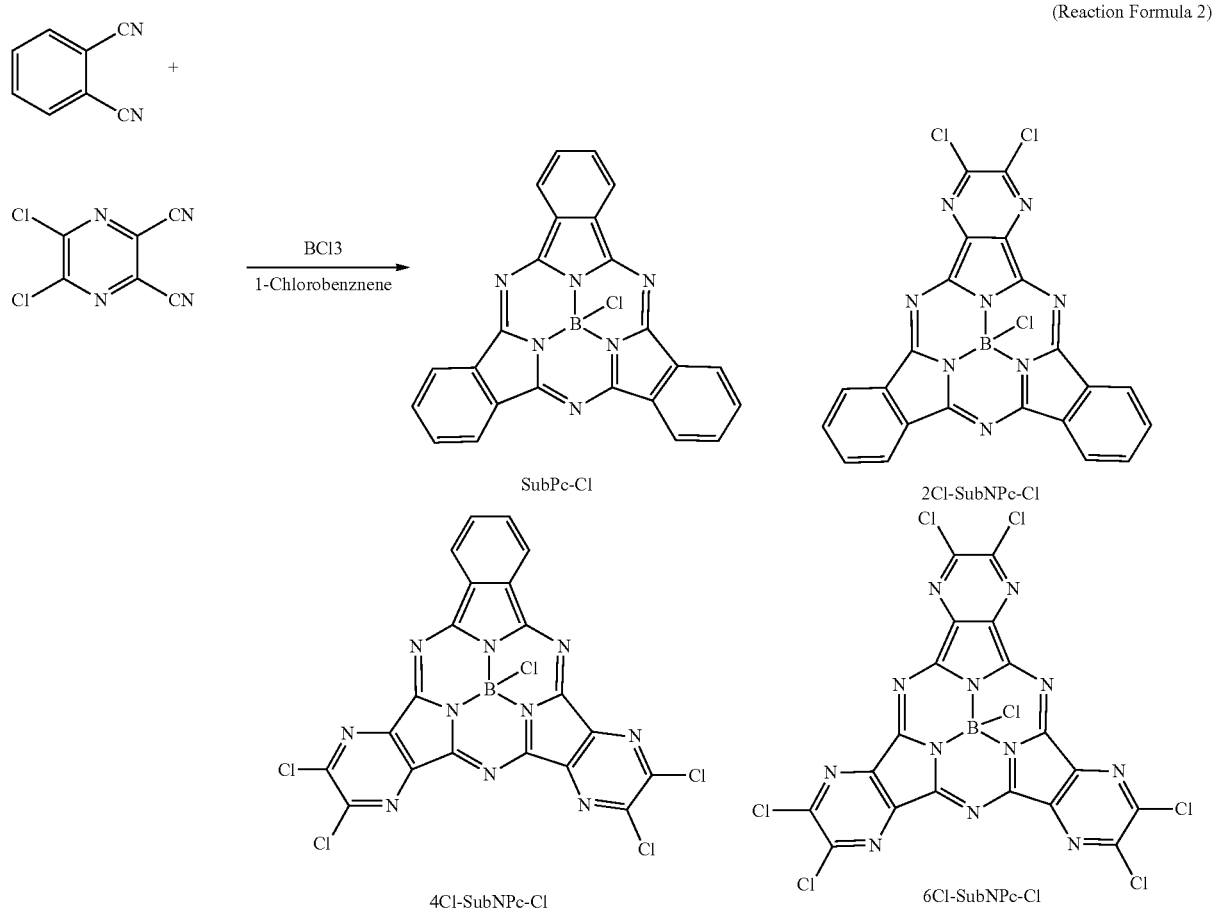

A mixture at 3 mmol of phthalonitrile and 5,6-dichloro-2,3-dicyanopyrazine (molar ratio 1:1) and boron trichloride (a dichloromethane solution) at 1 mmol (1 ml) were added to a flask and heated to reflux using 3 ml of 1-chlorobenzene in a solvent. A Dimroth cooler was connected to the mouth of the flask, an upper portion of the Dimroth cooler was additionally guided to an exhaust port of a draft by a rubber tube, and a low boiling point component was gradually evaporated. The flask had a bath temperature that was set to 190° C. and heated to reflux for about 16 hours.

After being heated to reflux, the mixture was left overnight, filtered, and further washed with dichloromethane. A filtrate was purified by column chromatography, and thus four types of derivatives (SubPc-Cl, 2Cl-SubNPc-Cl, 4Cl-SubNPc-Cl, and 6Cl-SubNPc-Cl) in Reaction Formula 2 were obtained. According to the above-described synthesis method, it was possible to synthesize 2Cl-SubNPc-Cl and 4Cl-SubNPc-Cl having different ring structures of $R_1$ to $R_3$.

[Evaluation of Subphthalocyanine Derivative]

Next, spectral characteristics of SubNPc-Cl and 6Cl-SubNPc-Cl synthesized above were evaluated by a solution method. In addition, for comparison, spectral characteristics of SubPc-Cl were evaluated by a similar method.

Figure 4:
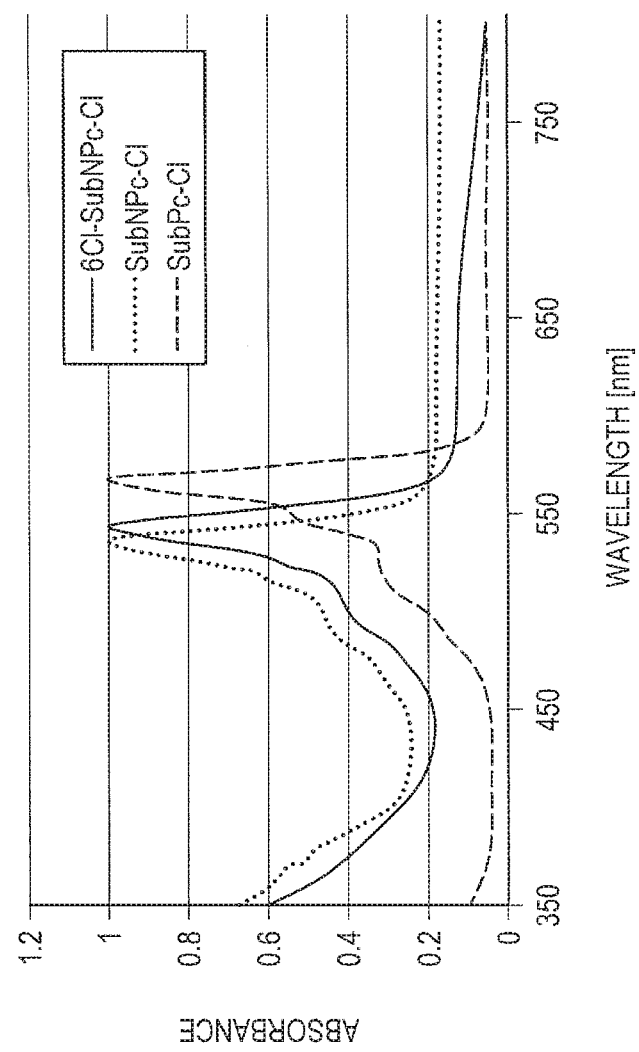
FIG. 4 is a graph showing an optical absorption spectrum of a subphthalocyanine derivative.

Specifically, each of the subphthalocyanine derivatives was dissolved in o-xylene, and an optical absorption spectrum was acquired by a visible-ultraviolet spectrophotometer using a quartz cell. The acquired optical absorption spectrums of the subphthalocyanine derivatives are shown in FIG. 4. The optical absorption spectrums shown in FIG. 4 are normalized such that an absorbance at a maximum absorption wavelength in each of the subphthalocyanine derivatives is 1.

As seen from the results shown in FIG. 4, it can be understood that SubNPc-Cl and 6Cl-SubNPc-Cl that are the subphthalocyanine derivatives according to an embodiment of the present disclosure have a shorter maximum absorption wavelength than SubPc-Cl according to a comparative example. In addition, it can be understood that tendencies of measured maximum absorption wavelengths of 6Cl-SubNPc-Cl and SubPc-Cl match tendencies of maximum absorption wavelengths of Example 5 and Comparative Example 1 of the above simulation analysis and the above simulation analysis is appropriate.

[Evaluation of Photoelectric Conversion Element]

In addition, 6Cl-SubNPc-Cl synthesized as above was used to manufacture a photoelectric conversion element according to an embodiment of the present disclosure and it was determined that the photoelectric conversion element functioned as a photoelectric conversion element.

Example 9

First, indium tin oxide (ITO) was formed into a film of 100 nm on a quartz substrate by a sputtering method, and the formed ITO thin film was patterned by photolithography and then etched to form a transparent lower electrode. Next, the formed transparent electrode was washed through UV/ozone treatment, a shadow mask was used to perform vacuum deposition such that a film formation ratio of 6Cl-SubNPc-Cl and quinacridone became 1:1, and thus a photoelectric conversion layer was formed.

Subsequently, aluminum (Al) was vacuum-deposited on the photoelectric conversion layer using a shadow mask and thus an upper electrode was formed. According to the above manufacturing method, the photoelectric conversion element was manufactured.

[Chem. 12]

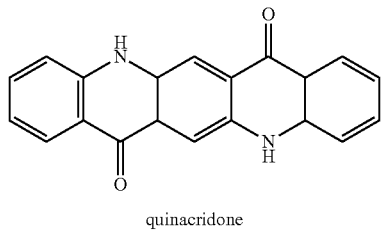

quinacridone

Subsequently, a photoelectric conversion function of the manufactured photoelectric conversion element according to Example 9 was evaluated. Specifically, a prober connected to a semiconductor parameter analyzer was used, a bias voltage was applied to an upper electrode and a lower electrode of the photoelectric conversion element according to Example 1, and a current value with and without illumination through a quartz substrate was measured.

Figure 5:
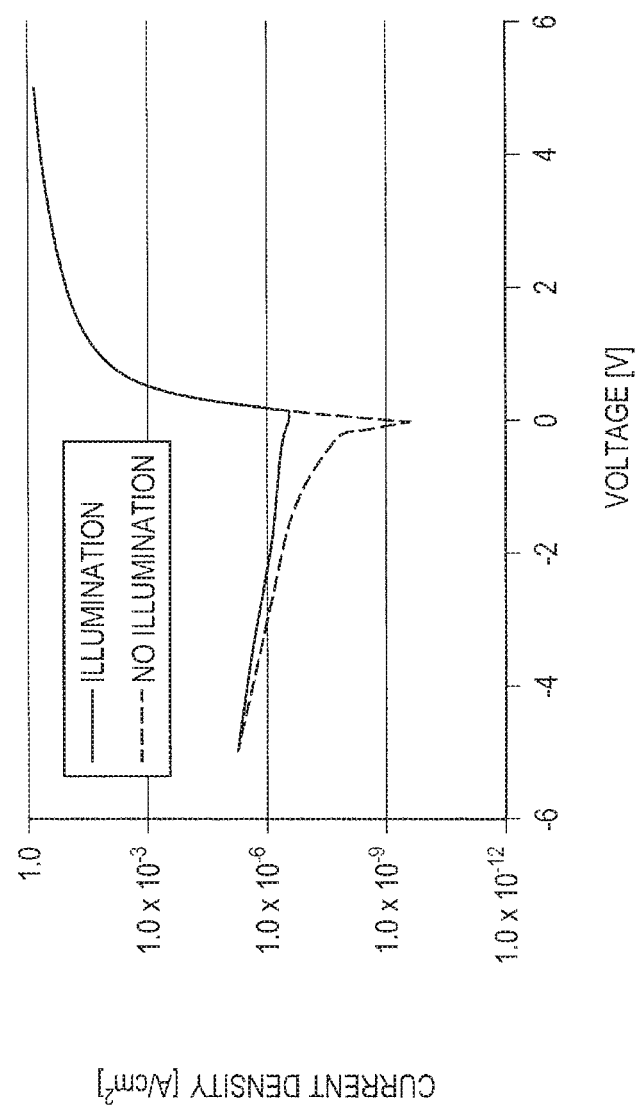
FIG. 5 is a graph showing changes in a current density of a photoelectric conversion element according to Example 9 with respect to a bias voltage.

The evaluation result of the photoelectric conversion function of the photoelectric conversion element according to Example 9 is shown in FIG. 5. FIG. 5 is a graph showing changes in a current density of the photoelectric conversion element according to Example 9 with respect to a bias voltage.

As seen from the results shown in FIG. 5, it can be understood that, in the photoelectric conversion element according to Example 9, in a bias voltage range of 0 to −3 V, a current density under illumination increases more than a current density with no illumination, and the photoelectric conversion function is provided. Accordingly, it can be understood that the subphthalocyanine derivative according to an embodiment of the present disclosure can be appropriately used as a photoelectric conversion material included in the photoelectric conversion film.

As can be understood from the above result, when the photoelectric conversion film according to an embodiment of the present disclosure includes the subphthalocyanine derivative represented by General Formula (1), it is possible to reduce absorption of light of a long wavelength range and selectively absorb green light. Accordingly, it can be understood that the photoelectric conversion film according to an embodiment of the present disclosure can be appropriately used as the green photoelectric conversion element of the solid-state image sensor and can increase an imaging characteristic of the solid-state image sensor.

3. Application Example of Photoelectric Conversion Element According to an Embodiment of the Present Disclosure Hereinafter, an application example of the photoelectric conversion element including the photoelectric conversion film according to an embodiment of the present disclosure will be described with reference to FIGS. 6 to 8.

[3.1. Configuration of Solid-State Image Sensor]

Figure 6:
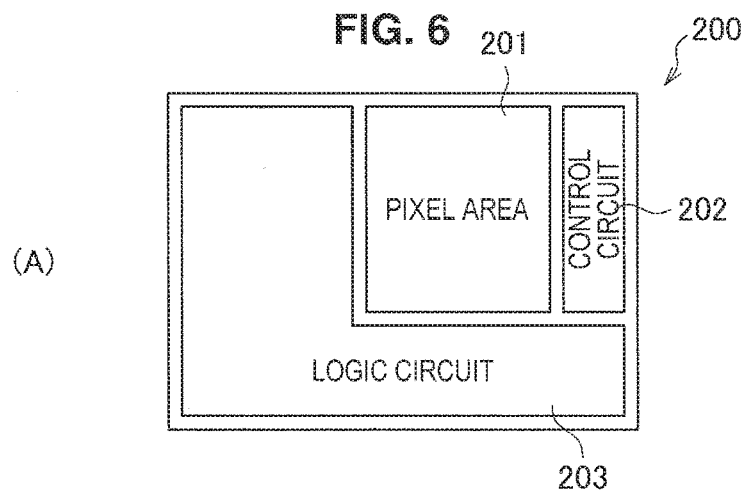
FIG. 6 shows schematic diagrams illustrating a structure of a solid-state image sensor to which a photoelectric conversion element according to an embodiment of the present disclosure is applied.
Figure 6:
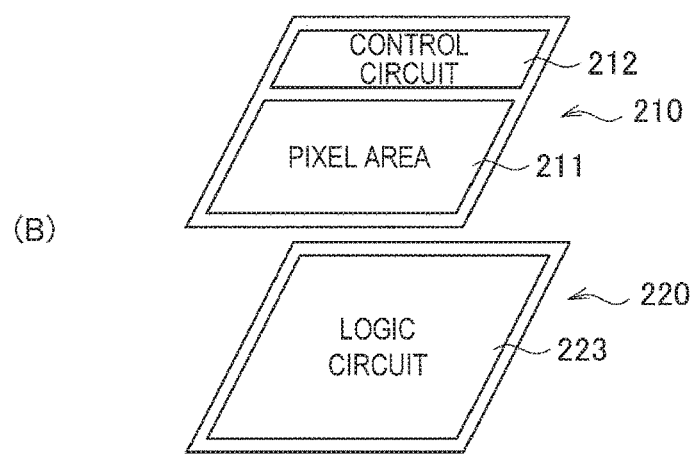
Figure 6:
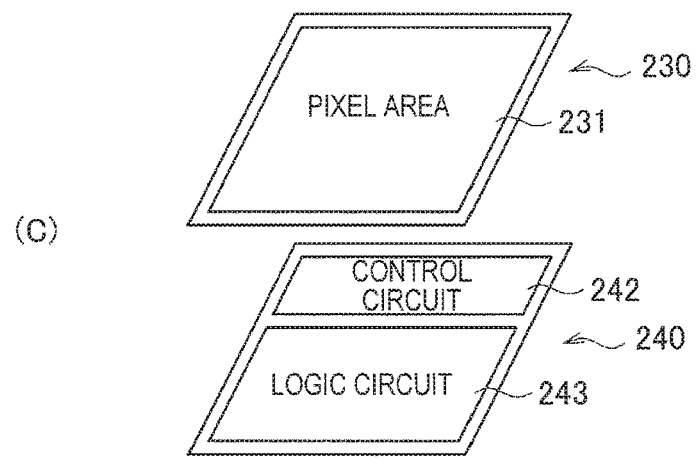

First, a configuration of the solid-state image sensor to which the photoelectric conversion element according to an embodiment of the present disclosure is applied will be described with reference to FIGS. 6 and 7. FIG. 6 is a schematic diagram illustrating a structure of a solid-state image sensor to which the photoelectric conversion element according to an embodiment of the present disclosure is applied.

Here, in FIG. 6, pixel areas 201, 211 and 231 are areas in which the photoelectric conversion element including the photoelectric conversion film according to an embodiment of the present disclosure are disposed. In addition, control circuits 202, 212 and 242 are arithmetic processing circuits configured to control each component of the solid-state image sensor. Logic circuits 203, 223 and 243 are signal processing circuits configured to process a signal obtained by photoelectric conversion of the photoelectric conversion element in the pixel area.

For example, as illustrated in FIG. 6A, in the solid-state image sensor to which the photoelectric conversion element according to an embodiment of the present disclosure is applied, the pixel area 201, the control circuit 202 and the logic circuit 203 may be formed in one semiconductor chip 200.

In addition, as illustrated in FIG. 6B, the solid-state image sensor to which the photoelectric conversion element according to an embodiment of the present disclosure is applied may be a laminated type solid-state image sensor in which the pixel area 211 and the control circuit 212 are formed in a first semiconductor chip 210, and the logic circuit 223 is formed in a second semiconductor chip 220.

Further, as illustrated in FIG. 6C, the solid-state image sensor to which the photoelectric conversion element according to an embodiment of the present disclosure is applied may be a laminated type solid-state image sensor in which the pixel area 231 is formed in a first semiconductor chip 230 and the control circuit 242 and the logic circuit 243 are formed in a second semiconductor chip 240.

In the solid-state image sensors illustrated in FIG. 6B and FIG. 5C, the pixel area is formed in a separate semiconductor chip from the semiconductor chip in which at least one of the control circuit and the logic circuit is formed. Accordingly, since the solid-state image sensors illustrated in FIG. 6B and FIG. 5C can extend the pixel area more than the solid-state image sensor illustrated in FIG. 6A, the number of pixels accommodated in the pixel area is increased. Therefore, it is possible to increase a plane resolution of the solid-state image sensors. For this reason, it is more preferable that the solid-state image sensor to which the photoelectric conversion element according to an embodiment of the present disclosure is applied be the laminated type solid-state image sensor illustrated in FIG. 6B and FIG. 5C.

Subsequently, a specific structure of a solid-state image sensor to which the photoelectric conversion element according to an embodiment of the present disclosure is applied will be described with reference to FIG. 7. FIG. 7 is a cross sectional view illustrating an outline structure of a unit pixel of a solid-state image sensor to which the photoelectric conversion element according to an embodiment of the present disclosure is applied. In addition, a solid-state image sensor 300 illustrated in FIG. 7 is a rear surface irradiation type solid-state image sensor in which light is incident from a surface opposite to a surface in which a pixel transistor and the like are formed. In addition, with respect to the drawing, an upper side is a light receiving surface, and a lower side is a circuit forming surface in which the pixel transistor and a peripheral circuit are formed.

Figure 7:
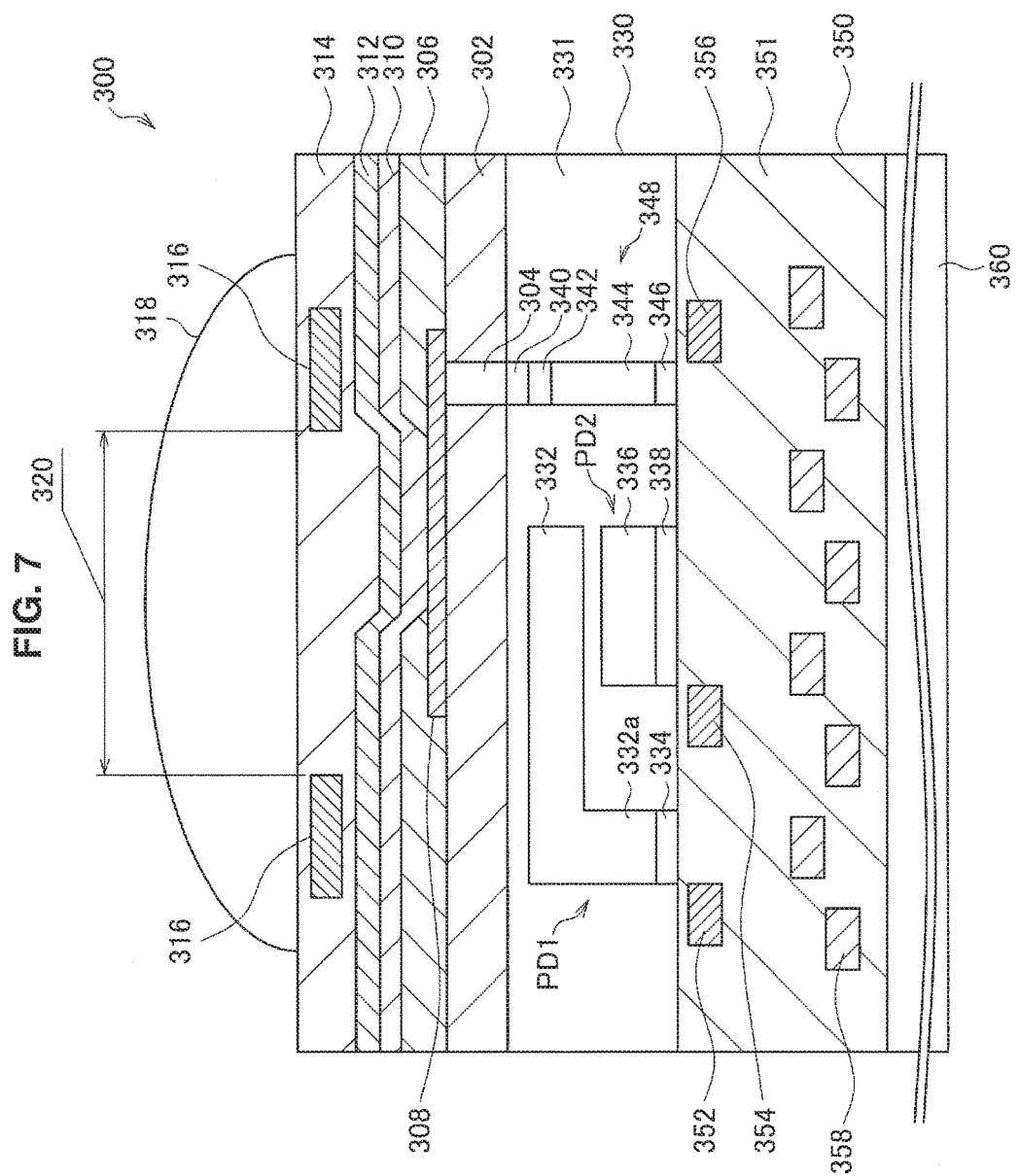
FIG. 7 is a cross-sectional view illustrating a schematic structure in a unit pixel of a solid-state image sensor to which a photoelectric conversion element according to an embodiment of the present disclosure is applied.

As illustrated in FIG. 7, the solid-state image sensor 300 has a configuration in which, in a photoelectric conversion area 320, a photoelectric conversion element including a first photodiode PD1 formed in a semiconductor substrate 330, a photoelectric conversion element including a second photodiode PD2 formed in the semiconductor substrate 330 and a photoelectric conversion element including an organic photoelectric conversion film 310 formed at a rear surface side of the semiconductor substrate 330 are laminated in a direction of incidence of light.

The first photodiode PD1 and the second photodiode PD2 are formed in a well area 331 that is a first conductivity type (for example, a p type) semiconductor area of the semiconductor substrate 330 made of silicon.

The first photodiode PD1 includes an n type semiconductor area 332 according to a second conductivity type (for example, an n type) impurity formed at a light receiving surface side of the semiconductor substrate 330 and an extending portion 332*a* that is formed by extending a part thereof to reach a surface side of the semiconductor substrate 330. A high concentration p type semiconductor area 334 serving as a charge accumulation layer is formed on a surface of the extending portion 332*a*. In addition, the extending portion 332*a* is formed as an extraction layer for extracting a signal charge accumulated in the n type semiconductor area 332 of the first photodiode PD1 to a surface side of the semiconductor substrate 330.

The second photodiode PD2 includes an n type semiconductor area 336 formed at a light receiving surface side of the semiconductor substrate 330 and a high concentration p type semiconductor area 338 that is formed at a surface side of the semiconductor substrate 330 as a charge accumulation layer.

In the first photodiode PD1 and the second photodiode PD2, when the p type semiconductor area is formed at an interface of the semiconductor substrate 330, it is possible to suppress the dark current generated at the interface of the semiconductor substrate 330.

Here, the second photodiode PD2 formed in an area that is farthest from the light receiving surface is, for example, a red photoelectric conversion element that absorbs red light and performs photoelectric conversion. In addition, the first photodiode PD1 formed closer to the light receiving surface side than the second photodiode PD2 is, for example, a blue photoelectric conversion element that absorbs blue light and performs photoelectric conversion.

The organic photoelectric conversion film 310 is formed on a rear surface of the semiconductor substrate 330 through an antireflection film 302 and an insulation film 306. In addition, the organic photoelectric conversion film 310 is interposed between an upper electrode 312 and a lower electrode 308 to form the photoelectric conversion element. Here, the organic photoelectric conversion film 310 is, for example, an organic film that absorbs green light of a wavelength of greater than or equal to 450 nm and less than 600 nm and performs photoelectric conversion and is formed as the photoelectric conversion film according to an embodiment of the present disclosure described above. In addition, the upper electrode 312 and the lower electrode 308 are made of, for example, a transparent conductive material such as indium tin oxide (ITO) or indium zinc oxide (IZO).

In addition, the lower electrode 308 is connected to a vertical transfer path 348 that is formed from the rear surface side to the surface side of the semiconductor substrate 330 through a contact plug 304 penetrating the antireflection film 302. The vertical transfer path 348 is formed to have a structure in which a connecting portion 340, a potential barrier layer 342, a charge accumulation layer 344 and a p type semiconductor area 346 are laminated from the rear surface side of the semiconductor substrate 330.

The connecting portion 340 includes an n type impurity area of a high impurity concentration that is formed at the rear surface side of the semiconductor substrate 330 and is formed for an ohmic contact with the contact plug 304. The potential barrier layer 342 includes a p type impurity area of a low concentration and forms a potential barrier between the connecting portion 340 and the charge accumulation layer 344. The charge accumulation layer 344 accumulates a signal charge transmitted from the organic photoelectric conversion film 310 and is formed in an n type impurity area of a lower concentration than the connecting portion 340. In addition, the p type semiconductor area 346 of a high concentration is formed on a surface of the semiconductor substrate 330. With this p type semiconductor area 346, it is possible to suppress the dark current generated at the interface of the semiconductor substrate 330.

Here, at the surface side of the semiconductor substrate 330, a multilayer wiring layer 350 including wires 358 laminated in a plurality of layers is formed through an interlayer insulating layer 351. In addition, in the vicinity of the surface of the semiconductor substrate 330, read circuits 352, 354 and 356 corresponding to the first photodiode PD1, the second photodiode PD2 and the organic photoelectric conversion film 310 are formed. The read circuits 352, 354 and 356 read a signal output from each photoelectric conversion element and transmit the signal to the logic circuit (not illustrated). Further, a supporting substrate 360 is formed on a surface of the multilayer wiring layer 350.

On the other hand, at a light receiving surface side of the upper electrode 312, a light shielding film 316 is formed to shield the extending portion 332*a* of the first photodiode PD1 and the vertical transfer path 348. Here, a separate area between the light shielding films 316 is the photoelectric conversion area 320. In addition, an on-chip lens 318 is formed above the light shielding film 316 through a flattening film 314.

The solid-state image sensor 300 to which the photoelectric conversion element according to an embodiment of the present disclosure is applied has been described above. In addition, in the solid-state image sensor 300 to which the photoelectric conversion element according to an embodiment of the present disclosure is applied, since color separation is performed on a unit pixel in a longitudinal direction, a color filter and the like are not provided.

[3.2. Configuration of Electronic Device]

Figure 8:
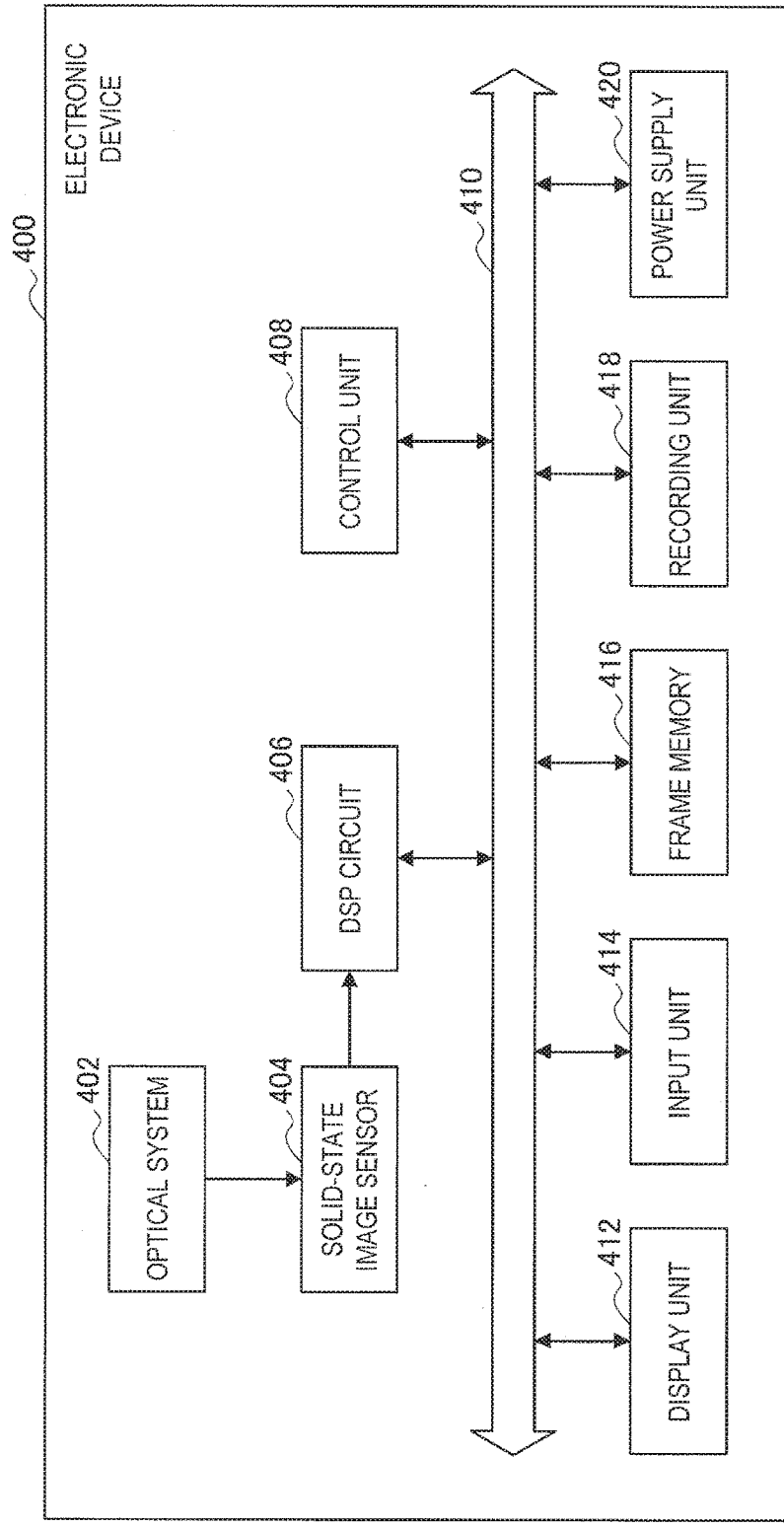
FIG. 8 is a block diagram illustrating a configuration of an electronic device to which a photoelectric conversion element according to an embodiment of the present disclosure is applied.

Next, a configuration of an electronic device to which the photoelectric conversion element according to an embodiment of the present disclosure is applied will be described with reference to FIG. 8. FIG. 8 is a block diagram illustrating a configuration of an electronic device to which the photoelectric conversion element according to an embodiment of the present disclosure is applied.

As illustrated in FIG. 8, an electronic device 400 includes an optical system 402, a solid-state image sensor 404, a digital signal processor (DSP) circuit 406, a control unit 408, an output unit 412, an input unit 414, a frame memory 416, a recording unit 418 and a power supply unit 420.

Here, the DSP circuit 406, the control unit 408, the output unit 412, the input unit 414, the frame memory 416, the recording unit 418 and the power supply unit 420 are connected to each other via a bus line 410.

The optical system 402 obtains incident light from an object and forms an image on an imaging surface of the solid-state image sensor 404. In addition, the solid-state image sensor 404 includes the photoelectric conversion element according to an embodiment of the present disclosure, converts an intensity of incident light focused on an imaging surface by the optical system 402 into an electrical signal in units of pixels, and outputs the result as a pixel signal.

The DSP circuit 406 processes the pixel signal transmitted from the solid-state image sensor 404 and outputs the result to the output unit 412, the frame memory 416, the recording unit 418 and the like. In addition, the control unit 408 includes, for example, an arithmetic processing circuit, and controls operations of each of the components of the electronic device 400.

The output unit 412 is, for example, a panel type display device such as a liquid crystal display and an organic electroluminescent display, and displays a video or a still image imaged by the solid-state image sensor 404. Here, the output unit 412 may also include a sound output device such as a speaker and a headphone. Here, the input unit 414 is, for example, a device for inputting a user's manipulation such as a touch panel and a button and issues manipulation commands for various functions of the electronic device 400 according to the user's manipulation.

The frame memory 416 temporarily stores the video, the still image and the like imaged by the solid-state image sensor 404. In addition, the recording unit 418 records the video, the still image and the like imaged by the solid-state image sensor 404 in a removable storage medium such as a magnetic disk, an optical disc, a magneto optical disc and a semiconductor memory.

The power supply unit 420 appropriately supplies various types of power serving as operating power of the DSP circuit 406, the control unit 408, the output unit 412, the input unit 414, the frame memory 416 and the recording unit 418 to these supply targets.

The electronic device 400 to which the photoelectric conversion element according to an embodiment of the present disclosure is applied has been described above. The electronic device 400 to which the photoelectric conversion element according to an embodiment of the present disclosure is applied may be, for example, an imaging apparatus.

4. Conclusion

As described above, when the photoelectric conversion film according to an embodiment of the present disclosure includes the subphthalocyanine derivative represented by General Formula (1), it is possible to reduce absorption of a long wavelength side and selectively absorb light of a green light range.

In addition, since the photoelectric conversion film according to an embodiment of the present disclosure can selectively absorb green light, it can be appropriately used as the green photoelectric conversion element of the solid-state image sensor. Accordingly, since the photoelectric conversion film according to an embodiment of the present disclosure can improve color separation of each color of light, it is possible to increase sensitivity of the solid-state image sensor and increase an imaging characteristic. In particular, since the photoelectric conversion film according to an embodiment of the present disclosure increases transparency of red light of a long wavelength side, it is possible to increase sensitivity of red light in the solid-state image sensor.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)
A photoelectric conversion film including:
a subphthalocyanine derivative represented by the following General Formula (1),

[Chem. 13]

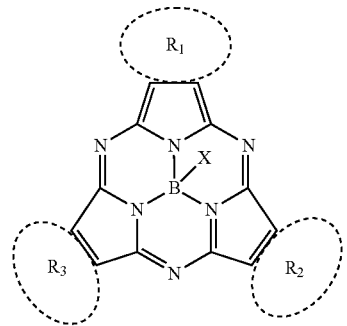

General Formula (1)

where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

(2)
The photoelectric conversion film according to (1), wherein at least one of $R_1$ to $R_3$ has a ring structure including a substituent.

(3)
The photoelectric conversion film according to (2),
wherein the substituent of $R_1$ to $R_3$ is a halogen.
(4)
The photoelectric conversion film according to any one of (1) to (3),
wherein $R_1$ to $R_3$ have a ring structure including a π-conjugated system structure.
(5)
The photoelectric conversion film according to any one of (1) to (4),
wherein $R_1$ to $R_3$ have a ring structure including 3 or more and 8 or fewer ring constituent atoms.
(6)
The photoelectric conversion film according to (5),
wherein $R_1$ to $R_3$ have a ring structure including 6 ring constituent atoms.
(7)
The photoelectric conversion film according to any one of (1) to (6),
wherein a hetero atom included in the ring structure of $R_1$ to $R_3$ is a nitrogen atom.
(8)
The photoelectric conversion film according to any one of (1) to (7),
wherein X is a halogen.
(9)
A solid-state image sensor including:
a photoelectric conversion film including a subphthalocyanine derivative represented by the following General Formula (1),

[Chem. 14]

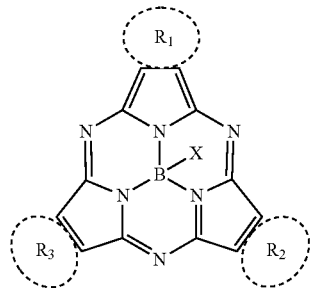

General Formula (1)

where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.
(10)
The solid-state image sensor according to (9),
wherein the photoelectric conversion film absorbs green light having a wavelength of greater than or equal to 450 nm and equal to or less than 600 nm and photoelectrically converts the absorbed green light.
(11)
The solid-state image sensor according to (9) or (10), configured as a laminated type solid-state image sensor, including:

a first chip in which the photoelectric conversion film is formed; and a second chip in which a signal processing circuit configured to process a signal that is obtained by photoelectric conversion by the photoelectric conversion film is formed, the second chip being laminated with the first chip.
(12)
An electronic device including:

a solid-state image sensor including a photoelectric conversion film including a subphthalocyanine derivative represented by the following General Formula (1);

an optical system configured to guide incident light to the solid-state image sensor; and an arithmetic processing circuit configured to perform arithmetic processing of an output signal from the solid-state image sensor,

[Chem. 15]

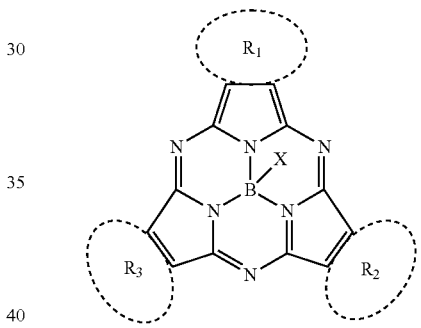

General Formula (1)

where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

REFERENCE SIGNS LIST 100 photoelectric conversion element
102 substrate
104 lower electrode
106 p buffer layer
108 photoelectric conversion layer
110 n buffer layer
112 upper electrode

What is claimed is:

1. A photoelectric conversion film, comprising:
a bulk hetero mixed layer, comprising:
a subphthalocyanine derivative represented by the following General Formula (1),

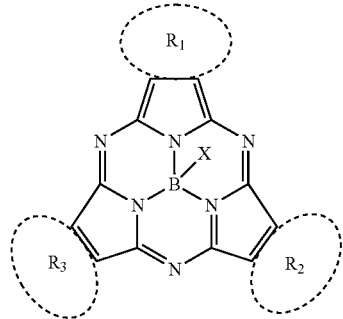

General Formula (1)

as a n-type light electric conversion material, where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

2. The photoelectric conversion film according to claim 1, wherein at least one of $R_1$ to $R_3$ has a ring structure including a substituent.

3. The photoelectric conversion film according to claim 2, wherein the substituent of $R_1$ to $R_3$ is a halogen.

4. The photoelectric conversion film according to claim 1, wherein $R_1$ to $R_3$ have a ring structure including a π-conjugated system structure.

5. The photoelectric conversion film according to claim 1, wherein $R_1$ to $R_3$ have a ring structure including 3 or more and 8 or fewer ring constituent atoms.

6. The photoelectric conversion film according to claim 5, wherein $R_1$ to $R_3$ have a ring structure including 6 ring constituent atoms.

7. The photoelectric conversion film according to claim 1, wherein a hetero atom included in the ring structure of $R_1$ to $R_3$ is a nitrogen atom.

8. The photoelectric conversion film according to claim 1, wherein X is a halogen.

9. A solid-state image sensor, comprising:
a photoelectric conversion film, comprising:
a bulk hetero mixed layer, comprising:
a subphthalocyanine derivative represented by the following General Formula (1),

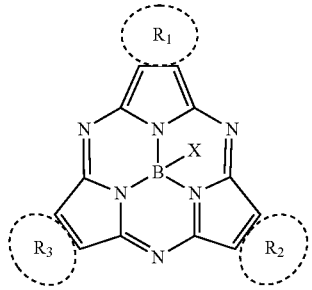

General Formula (1)

as a n-type light electric conversion material, where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

10. The solid-state image sensor according to claim 9, wherein the photoelectric conversion film absorbs green light having a wavelength of greater than or equal to 450 nm and equal to or less than 600 nm and photoelectrically converts the absorbed green light.

11. The solid-state image sensor according to claim 9, configured as a laminated type solid-state image sensor, comprising:
a first chip in which the photoelectric conversion film is formed; and
a second chip in which a signal processing circuit configured to process a signal that is obtained by photoelectric conversion by the photoelectric conversion film is formed, the second chip being laminated with the first chip.

12. An electronic device, comprising:
a solid-state image sensor, comprising;
a photoelectric conversion film, comprising:
a bulk hetero mixed layer, comprising:
a subphthalocyanine derivative represented by the following General Formula (1);
an optical system configured to guide incident light to the solid-state image sensor; and
an arithmetic processing circuit configured to perform arithmetic processing of an output signal from the solid-state image sensor,

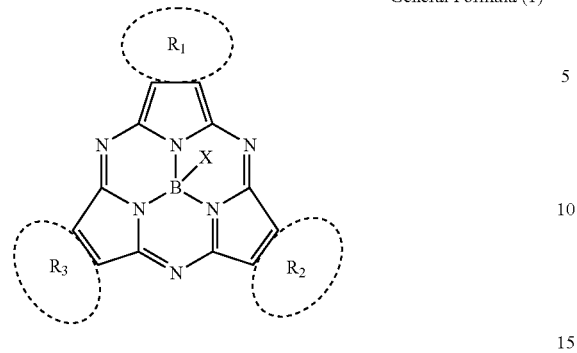

General Formula (1)

as a n-type light electric conversion material, where, in General Formula (1),

X represents any substituent selected from among the group consisting of a halogen, a hydroxy group, a thiol group, an amino group, a substituted or unsubstituted alkoxy group, a substituted or unsubstituted aryloxy group, a substituted or unsubstituted alkyl group, a substituted or unsubstituted alkyl amine group, a substituted or unsubstituted aryl amine group, a substituted or unsubstituted alkylthio group and a substituted or unsubstituted arylthio group, $R_1$ to $R_3$ each independently represent a substituted or unsubstituted ring structure, and at least one of $R_1$ to $R_3$ includes at least one hetero atom in the ring structure.

* * * * *